United States Patent
Kennedy, II et al.

(10) Patent No.: US 9,307,893 B2
(45) Date of Patent: Apr. 12, 2016

(54) SPACE-OPTIMIZED VISUALIZATION CATHETER WITH CAMERA TRAIN HOLDER IN A CATHETER WITH OFF-CENTERED LUMENS

(71) Applicant: Cook Medical Technologies LLC, Bloomington, IN (US)

(72) Inventors: Kenneth C. Kennedy, II, Clemmons, NC (US); Travis E. Dillon, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 132 days.

(21) Appl. No.: 13/728,334

(22) Filed: Dec. 27, 2012

(65) Prior Publication Data

US 2013/0172674 A1 Jul. 4, 2013

Related U.S. Application Data

(60) Provisional application No. 61/581,394, filed on Dec. 29, 2011.

(51) Int. Cl.
*A61B 1/05* (2006.01)
*A61B 1/00* (2006.01)
*A61B 1/018* (2006.01)

(52) U.S. Cl.
CPC ............... *A61B 1/05* (2013.01); *A61B 1/0011* (2013.01); *A61B 1/018* (2013.01); *A61B 1/051* (2013.01); *Y10T 29/49002* (2015.01)

(58) Field of Classification Search
CPC ............ A61M 2025/0034; A61M 2025/0037; A61M 2025/0036

USPC .................. 600/106, 112, 123, 127, 177–178
See application file for complete search history.

(56) References Cited

U.S. PATENT DOCUMENTS

| 4,369,768 A | 1/1983 | Vukovic |
| 4,491,865 A | 1/1985 | Danna et al. |

(Continued)

FOREIGN PATENT DOCUMENTS

| EP | 0 497 347 | 8/1992 |
| EP | 1 247 484 | 10/2002 |

(Continued)

OTHER PUBLICATIONS

International Search Report and Written Opinion for PCT/US2012/071765, dated Mar. 25, 2013, 9 pages.

(Continued)

*Primary Examiner* — Anhtuan T Nguyen
*Assistant Examiner* — Rajaa El Alami
(74) *Attorney, Agent, or Firm* — Brinks Gilson & Lione

(57) ABSTRACT

Methods and apparatuses for space-optimized visualization catheters are provided. Some embodiments utilize complimentary metal-oxide-semi-conductor ("CMOS") technology integrated into a CMOS camera train holder system that may be a stand-alone component for use with a visualization catheter, such as a baby endoscope, or may be fabricated/extruded as a part of the catheter itself. Some embodiments of apparatuses, methods, and equivalents thereto provide better direct visual feedback to the medical personnel performing the procedure while providing a similarly-sized outer diameter visualization catheter device having an increased space therein for additional lumens and equipment or by reducing the overall outer diameter of the visualization catheter.

20 Claims, 23 Drawing Sheets

(56) References Cited

U.S. PATENT DOCUMENTS

| | | |
|---|---|---|
| 5,261,889 A | 11/1993 | Laine et al. |
| 5,273,537 A | 12/1993 | Haskvitz et al. |
| 5,419,312 A | 5/1995 | Arenberg et al. |
| 5,428,386 A | 6/1995 | D'Alfonso et al. |
| 5,483,951 A | 1/1996 | Frassica et al. |
| 5,492,131 A | 2/1996 | Galel |
| 5,544,660 A | 8/1996 | Crowley |
| 5,754,313 A | 5/1998 | Pelchy et al. |
| 5,854,533 A | 12/1998 | Pappalardo |
| 5,929,901 A | 7/1999 | Adair et al. |
| 5,986,693 A | 11/1999 | Adair et al. |
| 6,043,839 A | 3/2000 | Adair et al. |
| 6,066,090 A | 5/2000 | Yoon |
| 6,086,528 A | 7/2000 | Adair |
| 6,106,457 A | 8/2000 | Perkins et al. |
| 6,190,877 B1 | 2/2001 | Adair |
| 6,211,904 B1 | 4/2001 | Adair et al. |
| 6,221,007 B1 | 4/2001 | Green |
| 6,234,958 B1 | 5/2001 | Snoke et al. |
| 6,275,255 B1 | 8/2001 | Adair et al. |
| 6,296,608 B1 | 10/2001 | Daniels et al. |
| 6,310,642 B1 | 10/2001 | Adair et al. |
| 6,316,215 B1 | 11/2001 | Adair et al. |
| 6,352,503 B1 | 3/2002 | Matsui et al. |
| 6,387,043 B1 | 5/2002 | Yoon |
| 6,419,626 B1 | 7/2002 | Yoon |
| 6,424,369 B1 | 7/2002 | Adair et al. |
| 6,452,626 B1 | 9/2002 | Adair et al. |
| 6,615,073 B1 | 9/2003 | Panescu et al. |
| 6,736,773 B2 | 5/2004 | Wendlandt et al. |
| 6,770,027 B2 | 8/2004 | Banik et al. |
| 6,800,057 B2 | 10/2004 | Tsujita et al. |
| 6,835,173 B2 | 12/2004 | Couvillon, Jr. |
| 6,862,036 B2 | 3/2005 | Adair et al. |
| 6,885,394 B1 | 4/2005 | Noguchi |
| 6,899,672 B2 | 5/2005 | Chin et al. |
| 6,899,675 B2 | 5/2005 | Cline et al. |
| 6,908,427 B2 | 6/2005 | Fleener et al. |
| 6,982,740 B2 | 1/2006 | Adair et al. |
| 6,982,742 B2 | 1/2006 | Adair et al. |
| 6,997,871 B2 | 2/2006 | Sonnenschein et al. |
| 7,002,621 B2 | 2/2006 | Adair et al. |
| 7,004,900 B2 | 2/2006 | Wendlandt et al. |
| 7,029,435 B2 | 4/2006 | Nakao |
| 7,030,904 B2 | 4/2006 | Adair et al. |
| 7,097,615 B2 | 8/2006 | Banik et al. |
| 7,366,365 B2 | 4/2008 | Carver |
| 7,393,321 B2 | 7/2008 | Doguchi et al. |
| 7,413,543 B2 | 8/2008 | Banik et al. |
| 7,479,106 B2 | 1/2009 | Banik et al. |
| 7,486,985 B2 | 2/2009 | Marshik-Geurts et al. |
| 7,578,786 B2 | 8/2009 | Boulais et al. |
| 7,591,783 B2 | 9/2009 | Boulais et al. |
| 7,591,785 B2 | 9/2009 | Wendlandt et al. |
| 7,647,085 B2 | 1/2010 | Cane et al. |
| 7,658,710 B2 | 2/2010 | Ueno et al. |
| 7,662,089 B2 | 2/2010 | Okada et al. |
| 7,666,135 B2 | 2/2010 | Couvillon, Jr. |
| 7,722,534 B2 | 5/2010 | Cline et al. |
| 7,729,751 B2 | 6/2010 | Ayame et al. |
| 7,774,048 B2 | 8/2010 | Nakaoka et al. |
| 7,787,121 B2 | 8/2010 | Tsujita et al. |
| 7,789,826 B2 | 9/2010 | Sullivan et al. |
| 7,811,277 B2 | 10/2010 | Boulais |
| 7,817,267 B2 | 10/2010 | Carver |
| 7,846,091 B2 | 12/2010 | Fulghum |
| 7,846,107 B2 | 12/2010 | Hoffman et al. |
| 7,850,599 B2 | 12/2010 | Takeuchi et al. |
| 7,860,055 B2 | 12/2010 | Hayasaka |
| 7,892,169 B2 | 2/2011 | Gono et al. |
| 7,918,787 B2 | 4/2011 | Saadat |
| 7,922,650 B2 | 4/2011 | McWeeney et al. |
| 7,922,654 B2 | 4/2011 | Boutillette et al. |
| 7,933,079 B2 | 4/2011 | Ning et al. |
| 7,944,466 B2 | 5/2011 | Abe et al. |
| 7,945,077 B2 | 5/2011 | Demos |
| 7,955,255 B2* | 6/2011 | Boulais et al. ............... 600/177 |
| 7,965,878 B2 | 6/2011 | Higuchi et al. |
| 2002/0147383 A1 | 10/2002 | Weber et al. |
| 2003/0009161 A1 | 1/2003 | Messing et al. |
| 2003/0009162 A1 | 1/2003 | Messing et al. |
| 2003/0009163 A1 | 1/2003 | Messing et al. |
| 2004/0097803 A1 | 5/2004 | Panescu |
| 2004/0138525 A1 | 7/2004 | Saadat et al. |
| 2004/0199052 A1 | 10/2004 | Banik et al. |
| 2004/0249246 A1 | 12/2004 | Campos |
| 2005/0027163 A1 | 2/2005 | Chin et al. |
| 2005/0027164 A1 | 2/2005 | Barbato et al. |
| 2005/0038322 A1 | 2/2005 | Banik |
| 2005/0096502 A1 | 5/2005 | Khalili |
| 2005/0107741 A1 | 5/2005 | Willard et al. |
| 2005/0119527 A1 | 6/2005 | Banik et al. |
| 2005/0137459 A1 | 6/2005 | Chin et al. |
| 2005/0154262 A1 | 7/2005 | Banik et al. |
| 2005/0215859 A1 | 9/2005 | Chin et al. |
| 2005/0222499 A1 | 10/2005 | Banik et al. |
| 2005/0245789 A1 | 11/2005 | Smith et al. |
| 2006/0022234 A1 | 2/2006 | Adair et al. |
| 2006/0030753 A1 | 2/2006 | Boutillette et al. |
| 2006/0069312 A1 | 3/2006 | O'Connor |
| 2006/0178658 A1 | 8/2006 | Smith |
| 2006/0189845 A1 | 8/2006 | Maahs et al. |
| 2006/0252988 A1 | 11/2006 | Ayame et al. |
| 2006/0252993 A1 | 11/2006 | Freed et al. |
| 2006/0293563 A1 | 12/2006 | Banik et al. |
| 2007/0040906 A1 | 2/2007 | Iketani |
| 2007/0041720 A1 | 2/2007 | Iketani |
| 2007/0088193 A1 | 4/2007 | Omori et al. |
| 2007/0129605 A1 | 6/2007 | Schaaf |
| 2007/0153542 A1 | 7/2007 | Gono et al. |
| 2007/0167968 A1 | 7/2007 | Pandey |
| 2007/0185384 A1 | 8/2007 | Bayer et al. |
| 2007/0225559 A1 | 9/2007 | Clerc et al. |
| 2007/0249907 A1 | 10/2007 | Boulais et al. |
| 2007/0270650 A1 | 11/2007 | Eno et al. |
| 2008/0021274 A1* | 1/2008 | Bayer et al. ............... 600/112 |
| 2008/0027278 A1 | 1/2008 | Mizuno |
| 2008/0058591 A1 | 3/2008 | Saadat et al. |
| 2008/0081990 A1 | 4/2008 | Berenfeld et al. |
| 2008/0146877 A1 | 6/2008 | Matsuzawa et al. |
| 2008/0188866 A1* | 8/2008 | Karpiel et al. ............... 606/127 |
| 2008/0208006 A1 | 8/2008 | Farr |
| 2008/0239070 A1 | 10/2008 | Westwick et al. |
| 2008/0269561 A1 | 10/2008 | Banik et al. |
| 2008/0281154 A1 | 11/2008 | Gono et al. |
| 2008/0294105 A1 | 11/2008 | Gono et al. |
| 2009/0012368 A1 | 1/2009 | Banik |
| 2009/0023985 A1 | 1/2009 | Ewers |
| 2009/0023991 A1 | 1/2009 | Gono et al. |
| 2009/0036741 A1 | 2/2009 | Igarashi et al. |
| 2009/0054803 A1 | 2/2009 | Saadat et al. |
| 2009/0082625 A1 | 3/2009 | Gono |
| 2009/0118577 A9 | 5/2009 | Snay et al. |
| 2009/0127507 A1 | 5/2009 | Hiramatsu et al. |
| 2009/0131800 A1 | 5/2009 | Liang |
| 2009/0141125 A1 | 6/2009 | Yamazaki |
| 2009/0253959 A1 | 10/2009 | Yoshie et al. |
| 2009/0259097 A1 | 10/2009 | Thompson |
| 2009/0275798 A1 | 11/2009 | Naito |
| 2009/0287044 A1 | 11/2009 | Yamatani |
| 2009/0292175 A1 | 11/2009 | Akimoto et al. |
| 2009/0306476 A1 | 12/2009 | Banik et al. |
| 2009/0312645 A1 | 12/2009 | Weitzner et al. |
| 2009/0322907 A1 | 12/2009 | Takahashi |
| 2009/0326320 A1 | 12/2009 | Sinofsky et al. |
| 2010/0022824 A1 | 1/2010 | Cybulski et al. |
| 2010/0041947 A1 | 2/2010 | Wendlandt et al. |
| 2010/0048999 A1 | 2/2010 | Boulais et al. |
| 2010/0054576 A1 | 3/2010 | Tsujita |
| 2010/0069720 A1 | 3/2010 | Fulghum et al. |
| 2010/0076266 A1 | 3/2010 | Boulais et al. |
| 2010/0137688 A1 | 6/2010 | Couvillon, Jr. |
| 2010/0140461 A1 | 6/2010 | Sprigle et al. |
| 2010/0141747 A1 | 6/2010 | Kubo et al. |

(56) References Cited

U.S. PATENT DOCUMENTS

| | | |
|---|---|---|
| 2010/0158330 A1 | 6/2010 | Guissin et al. |
| 2010/0210905 A1 | 8/2010 | Takeuchi et al. |
| 2010/0249512 A1 | 9/2010 | McKinley et al. |
| 2010/0256448 A1 | 10/2010 | Smith et al. |
| 2010/0256449 A1 | 10/2010 | Kubo et al. |
| 2010/0256469 A1 | 10/2010 | Cook et al. |
| 2010/0286475 A1 | 11/2010 | Robertson |
| 2010/0309299 A1 | 12/2010 | Kubo et al. |
| 2011/0004058 A1 | 1/2011 | Oneda et al. |
| 2011/0069398 A1 | 3/2011 | Ning et al. |
| 2011/0071352 A1 | 3/2011 | Ozawa et al. |
| 2011/0071353 A1 | 3/2011 | Ozawa et al. |
| 2011/0077462 A1 | 3/2011 | Saitou et al. |
| 2011/0082337 A1 | 4/2011 | Boulais |
| 2011/0105839 A1 | 5/2011 | Hoffman et al. |
| 2011/0105844 A1 | 5/2011 | Sullivan et al. |
| 2011/0112362 A1 | 5/2011 | Minetoma |
| 2011/0115882 A1 | 5/2011 | Shahinian et al. |

FOREIGN PATENT DOCUMENTS

| | | |
|---|---|---|
| EP | 1 284 120 | 2/2003 |
| WO | WO 96/39918 | 12/1996 |
| WO | WO 98/14111 | 4/1998 |
| WO | WO 2005/016133 | 2/2005 |
| WO | WO 2005/115221 | 12/2005 |
| WO | WO 2007/133594 | 11/2007 |

OTHER PUBLICATIONS

International Search Report and Written Opinion for PCT/US2012/071785, dated Jun. 14, 2013, 13 pages.

International Search Report and Written Opinion for PCT/US2012/071930, dated Apr. 11, 2013, 10 pages.

International Search Report and Written Opinion for PCT/US2012/071935, dated Mar. 25, 2013, 9 pages.

\* cited by examiner

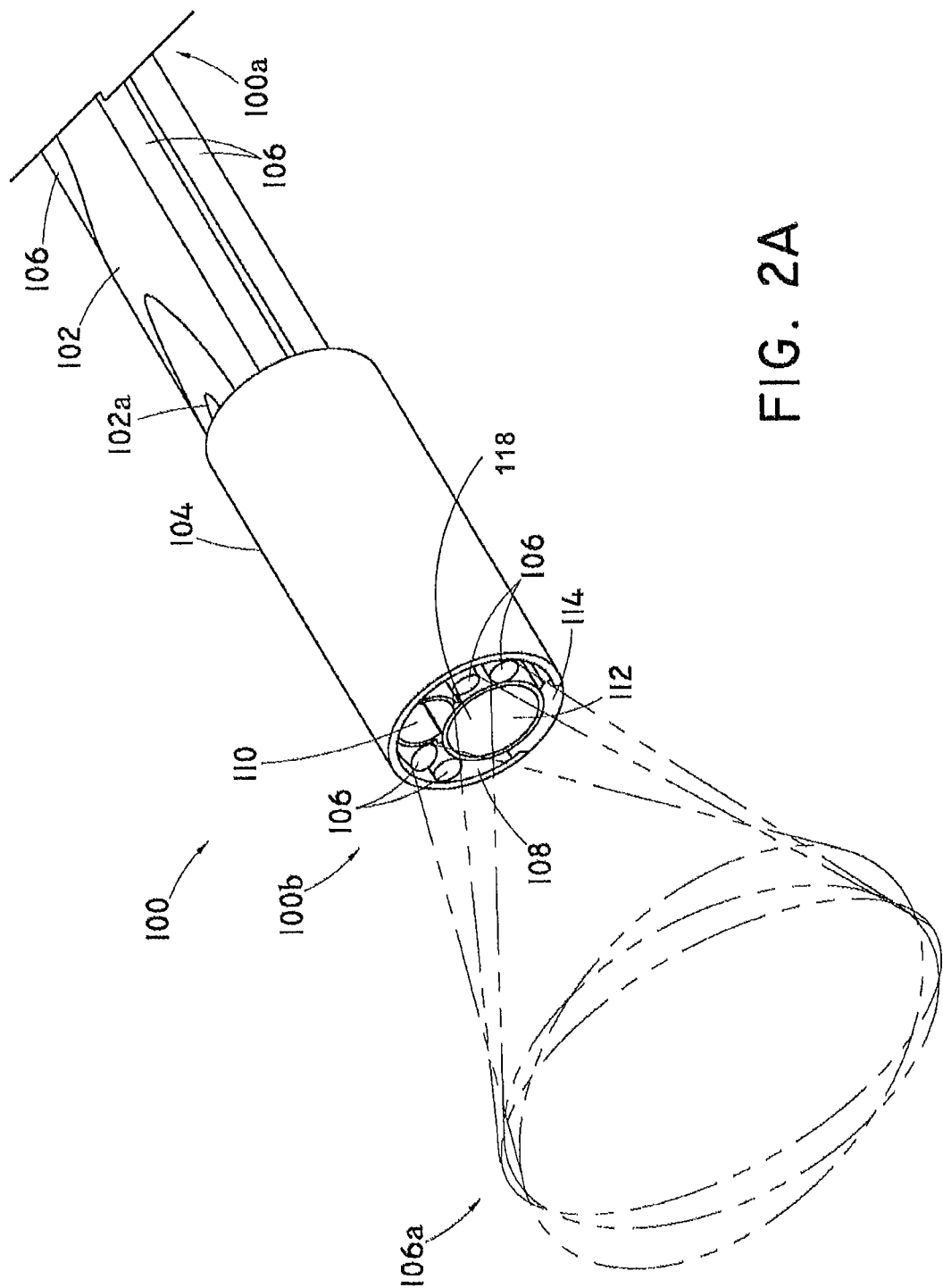

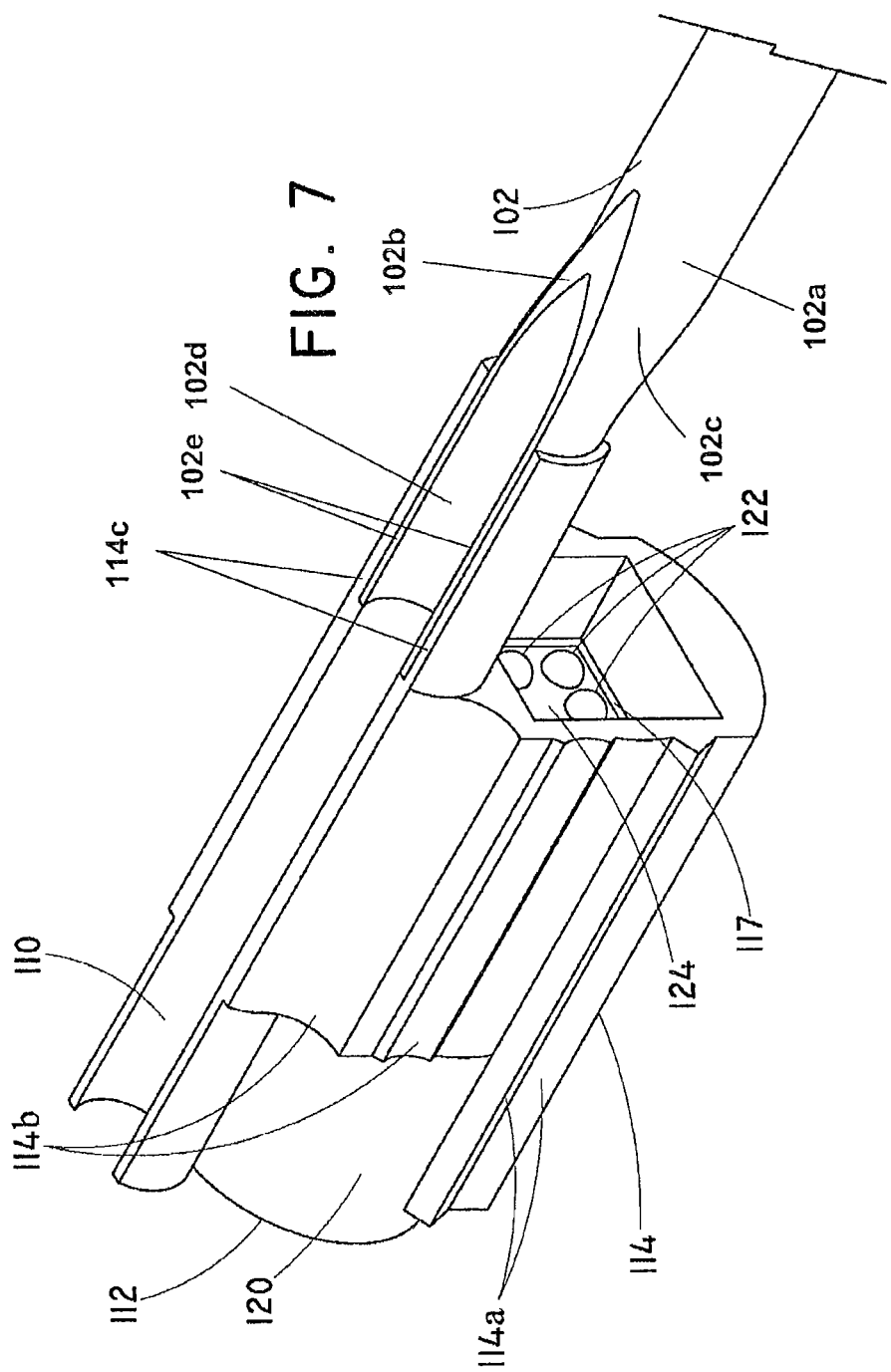

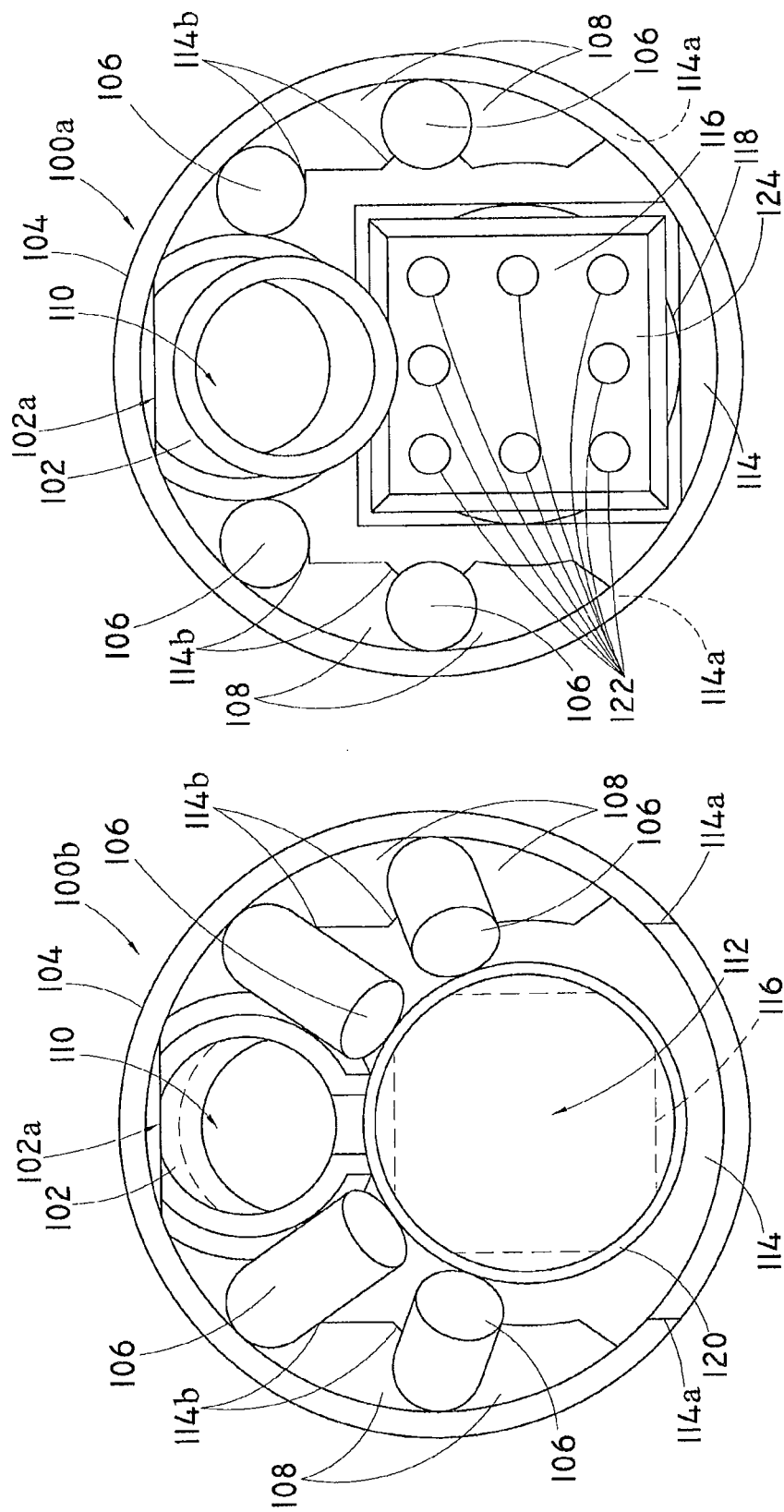

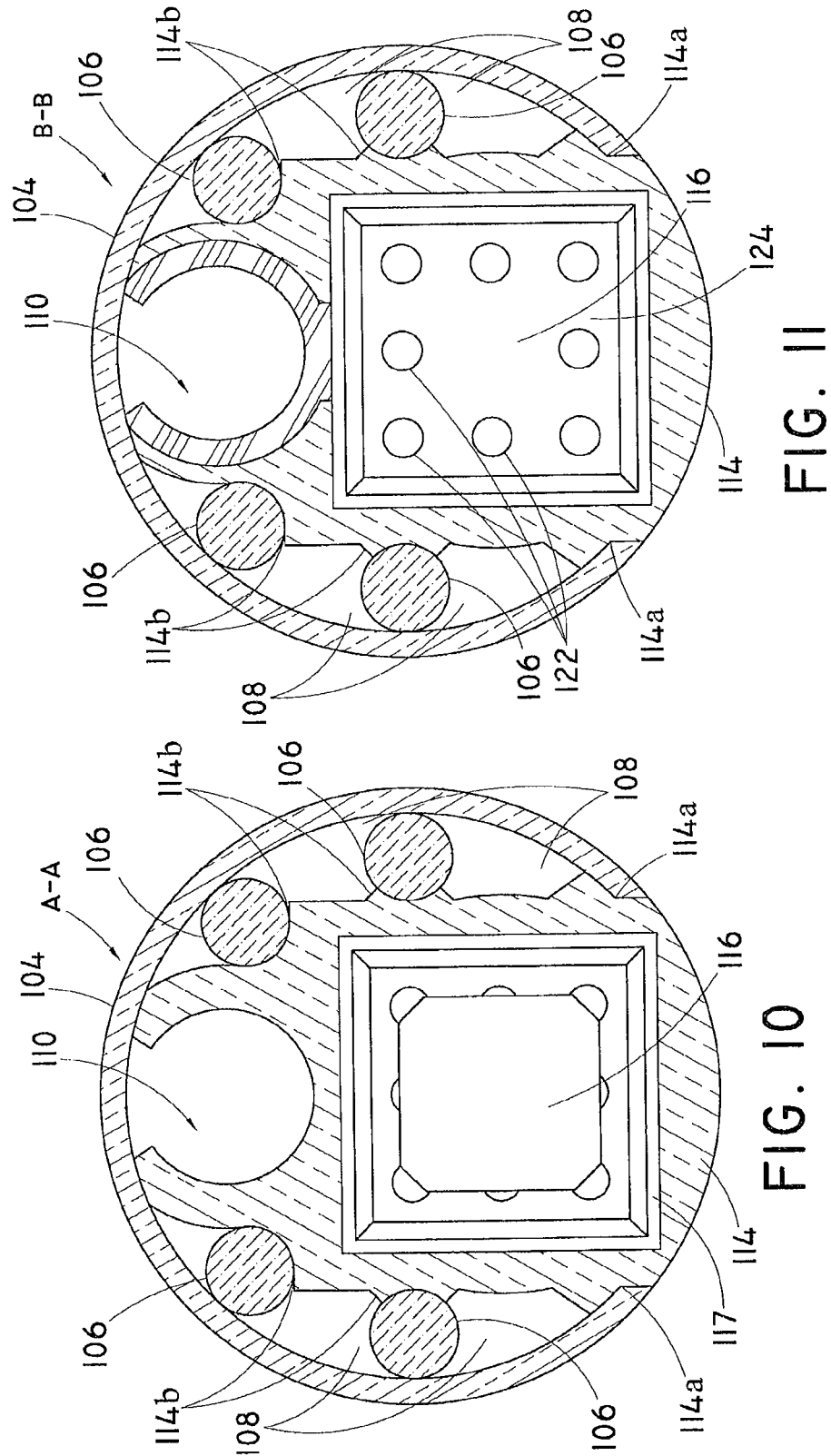

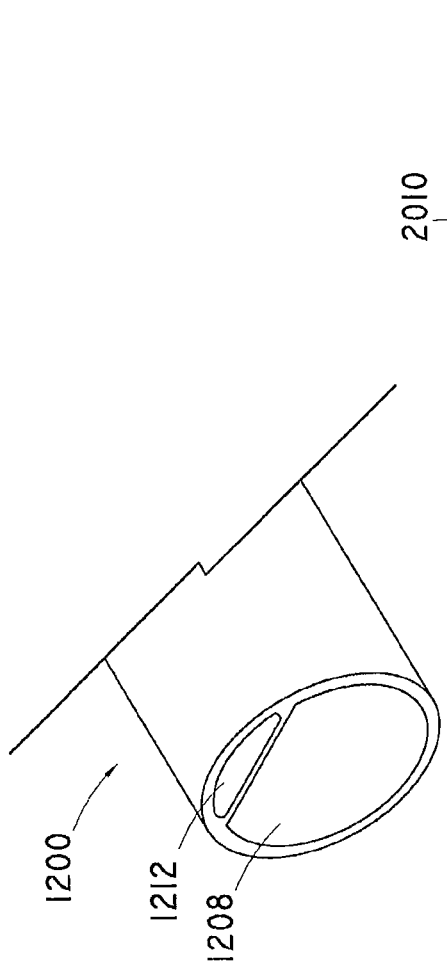
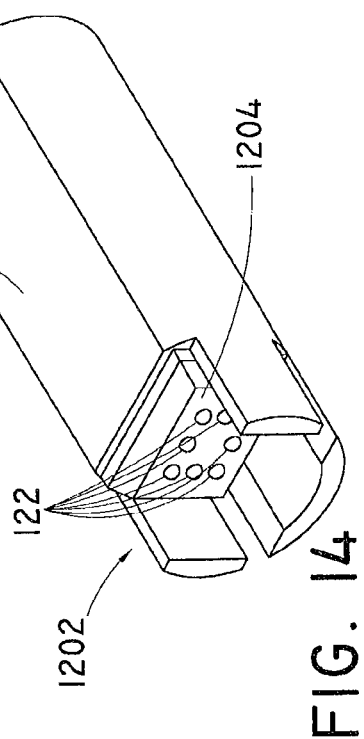
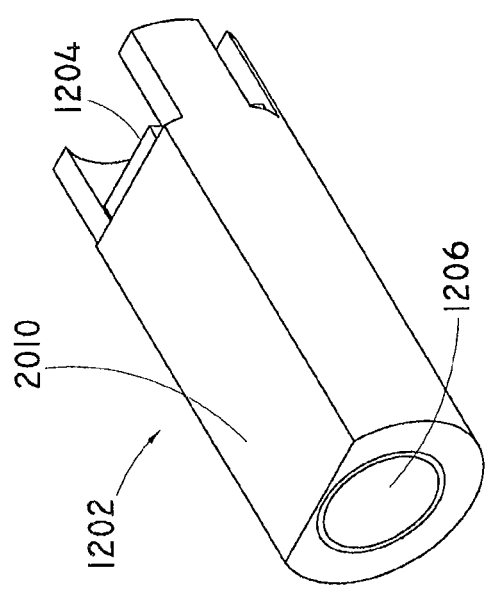

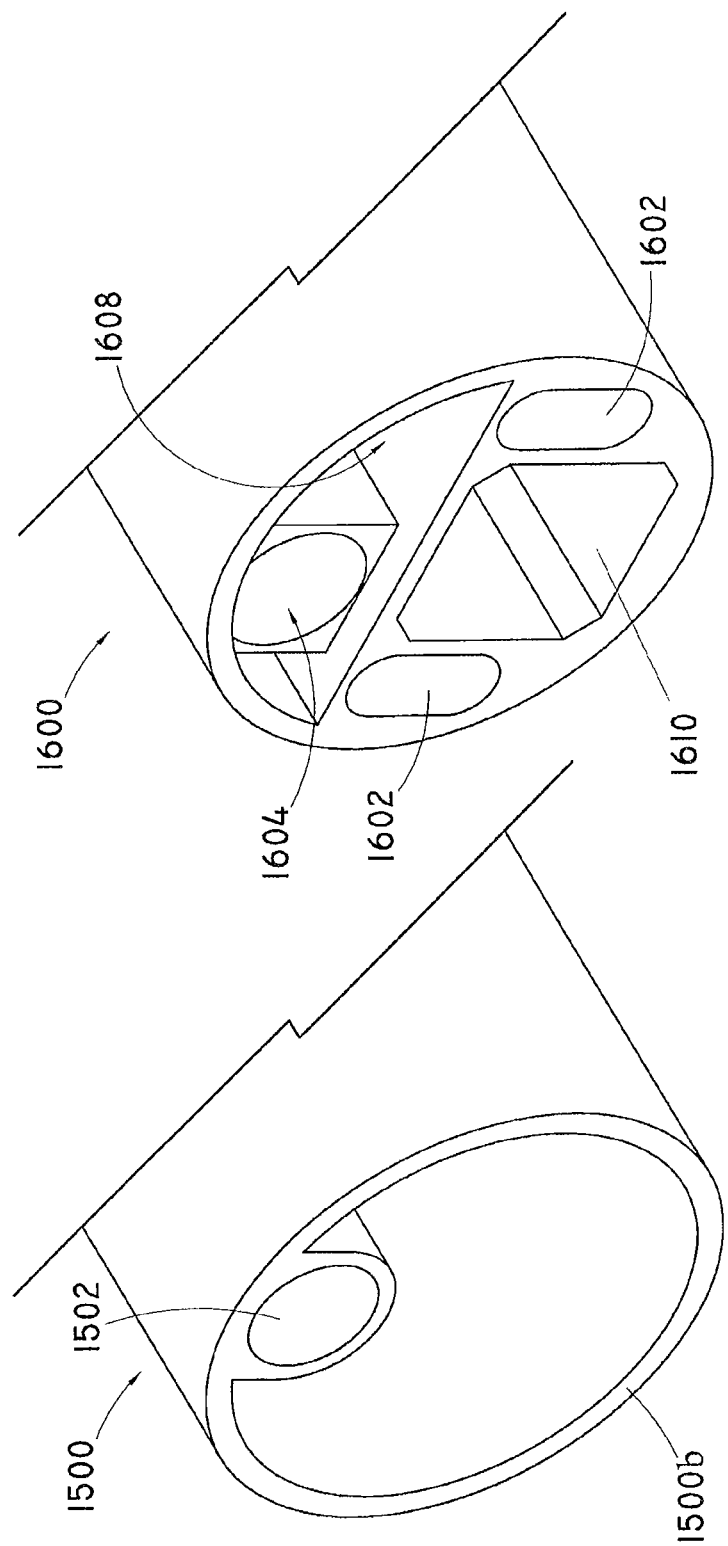

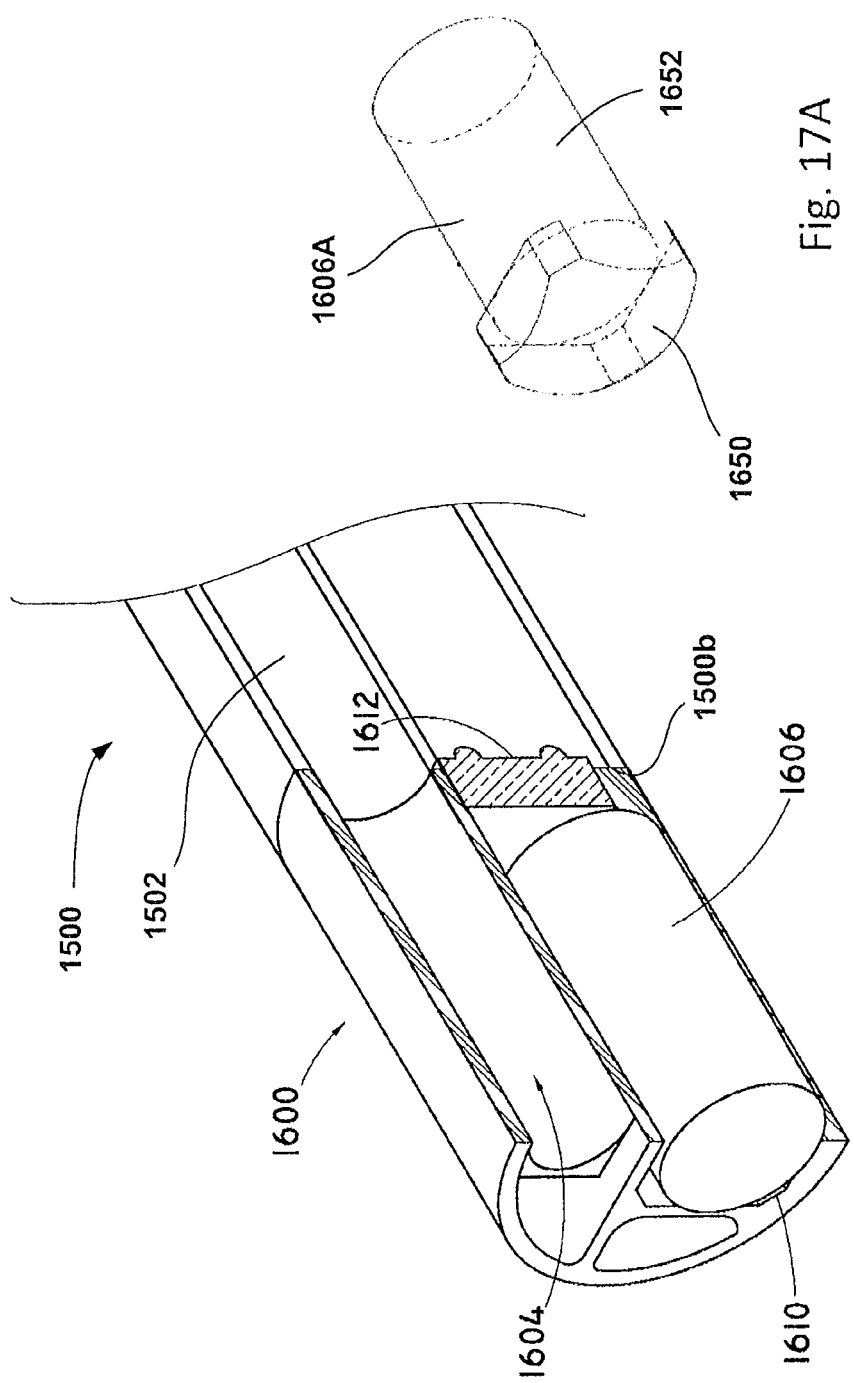

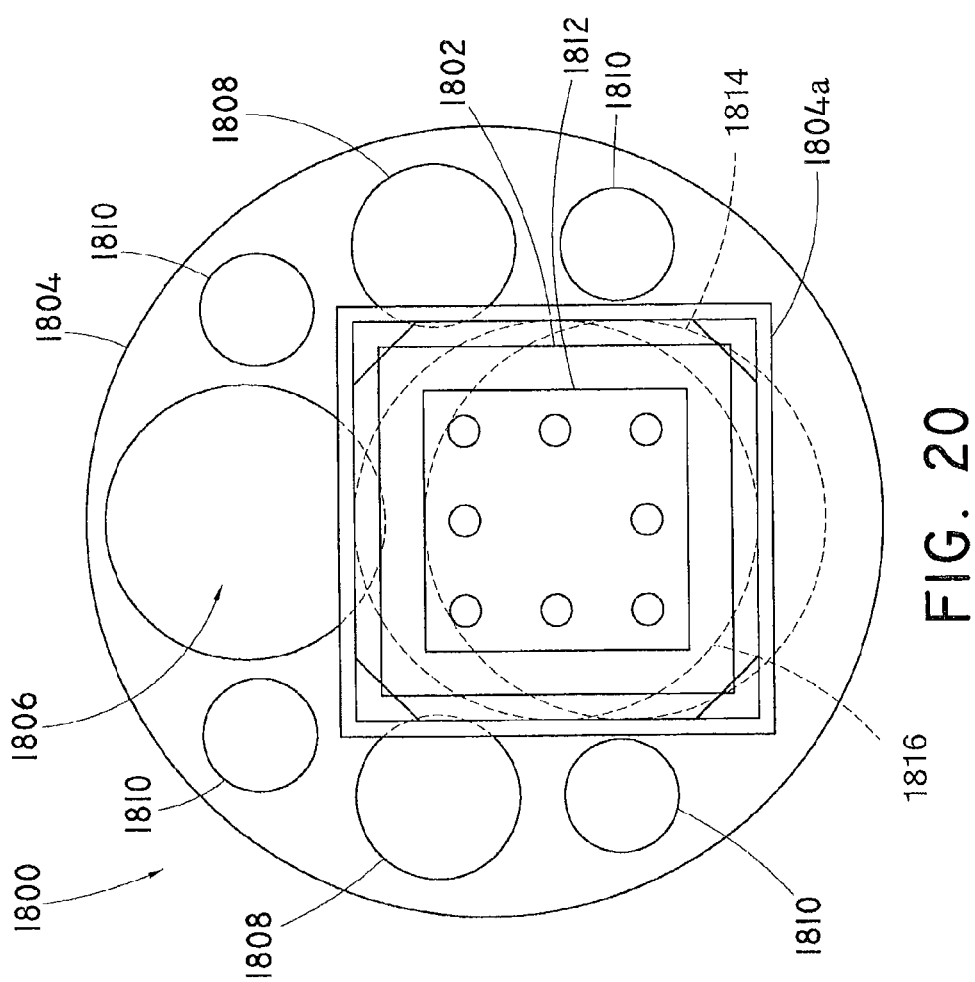

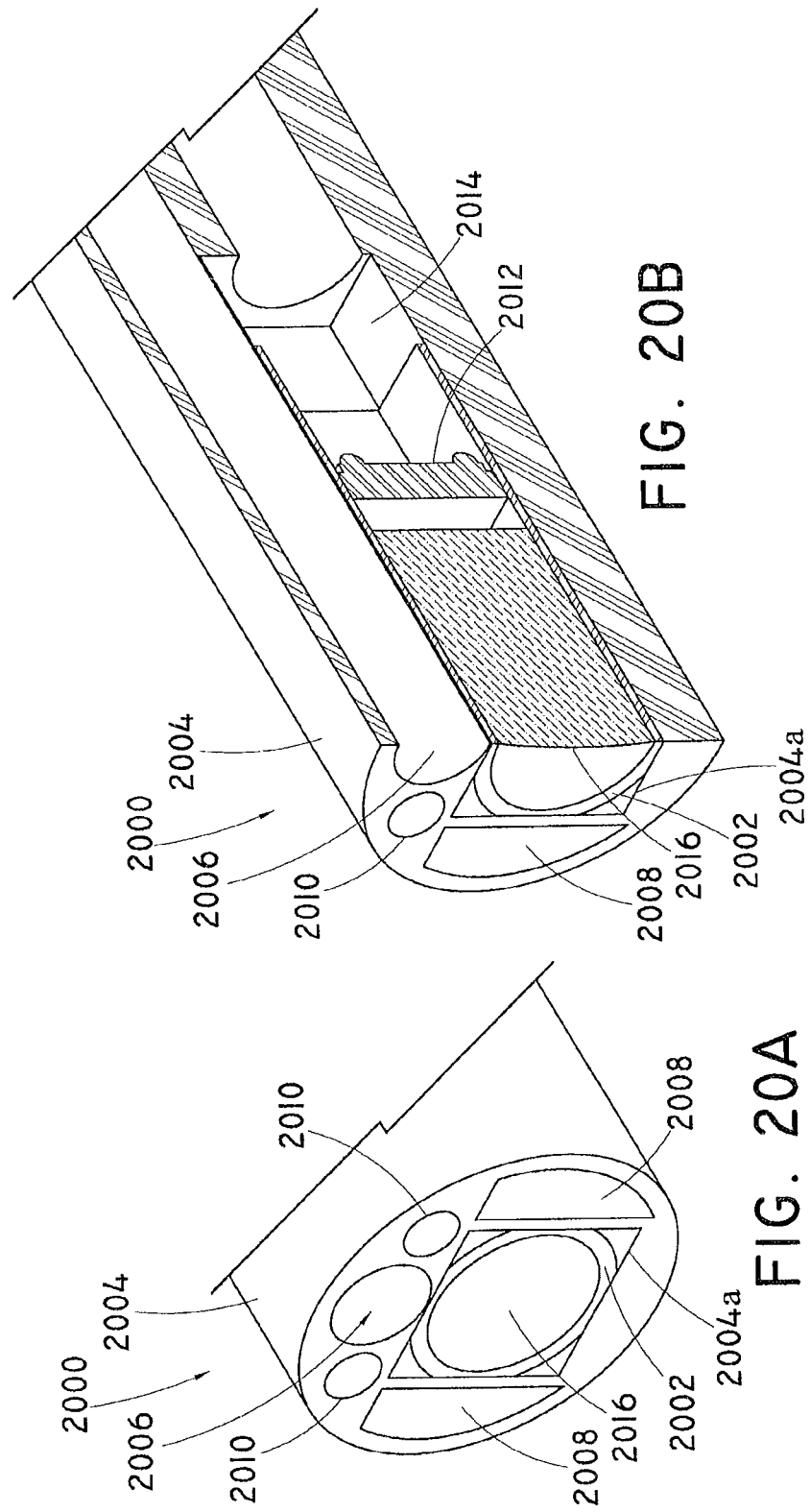

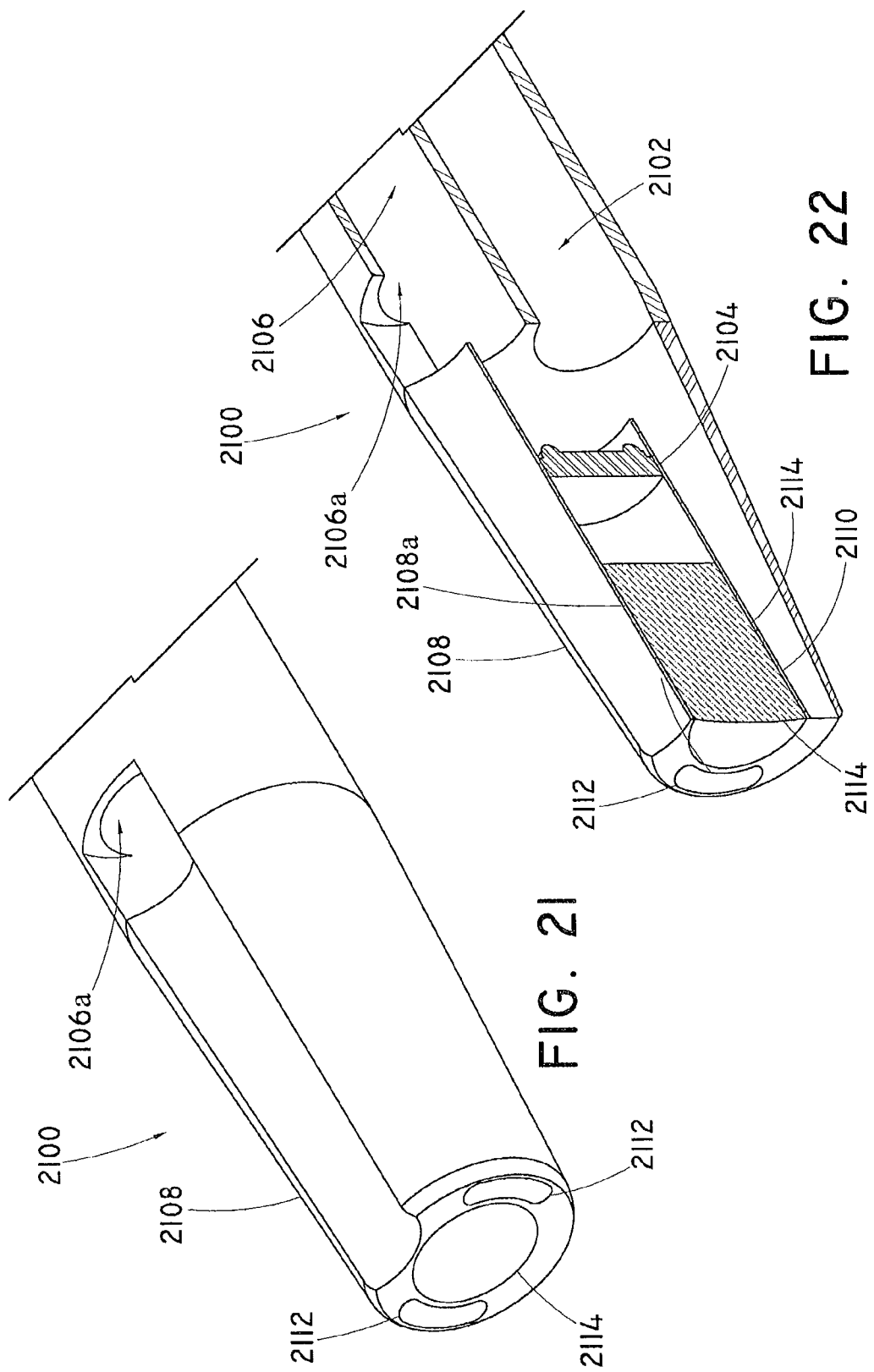

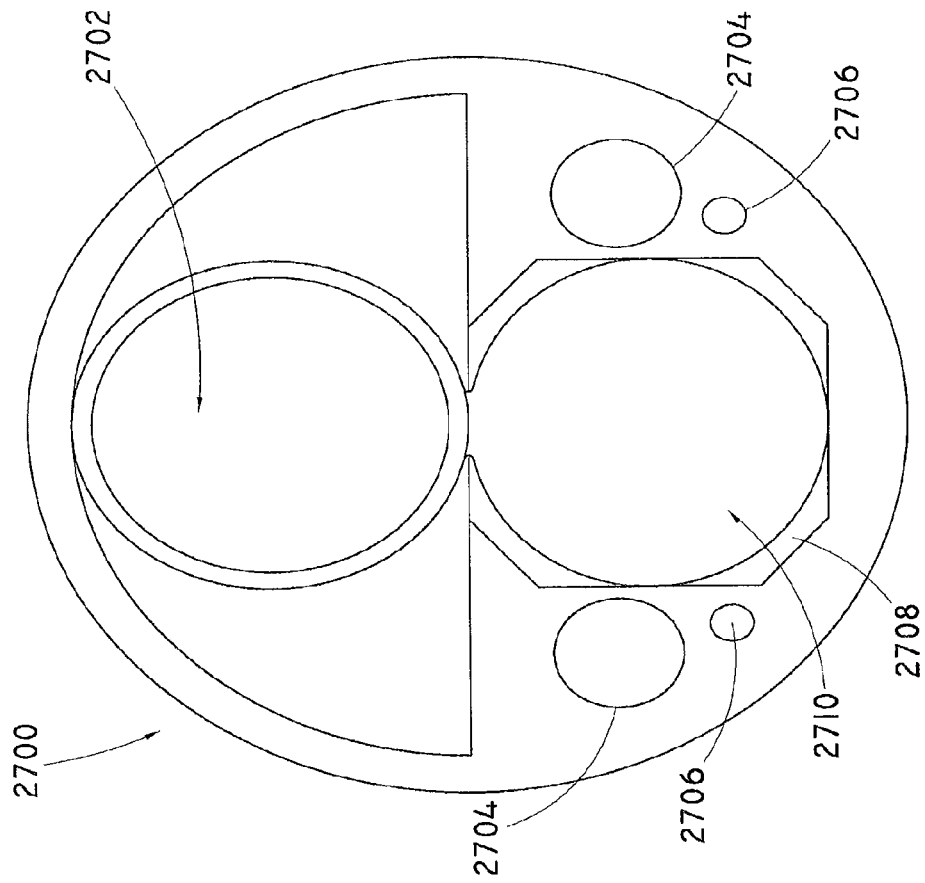
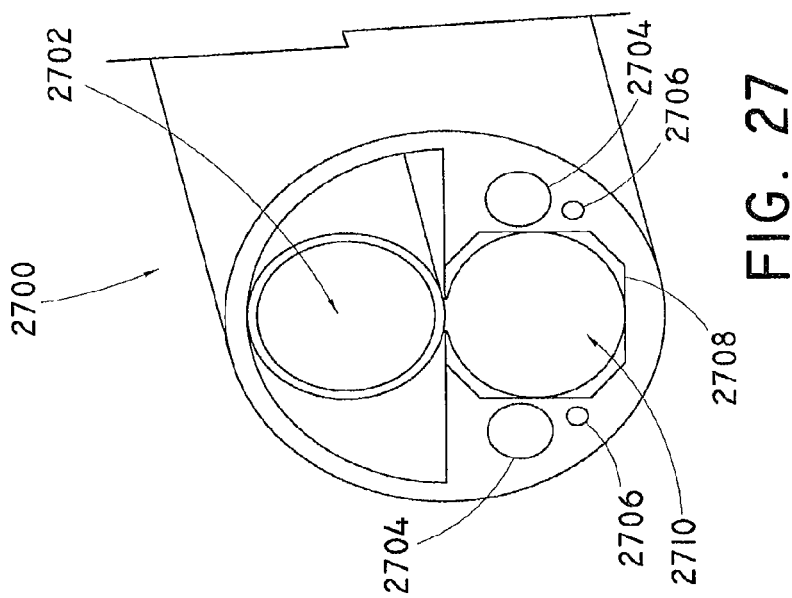

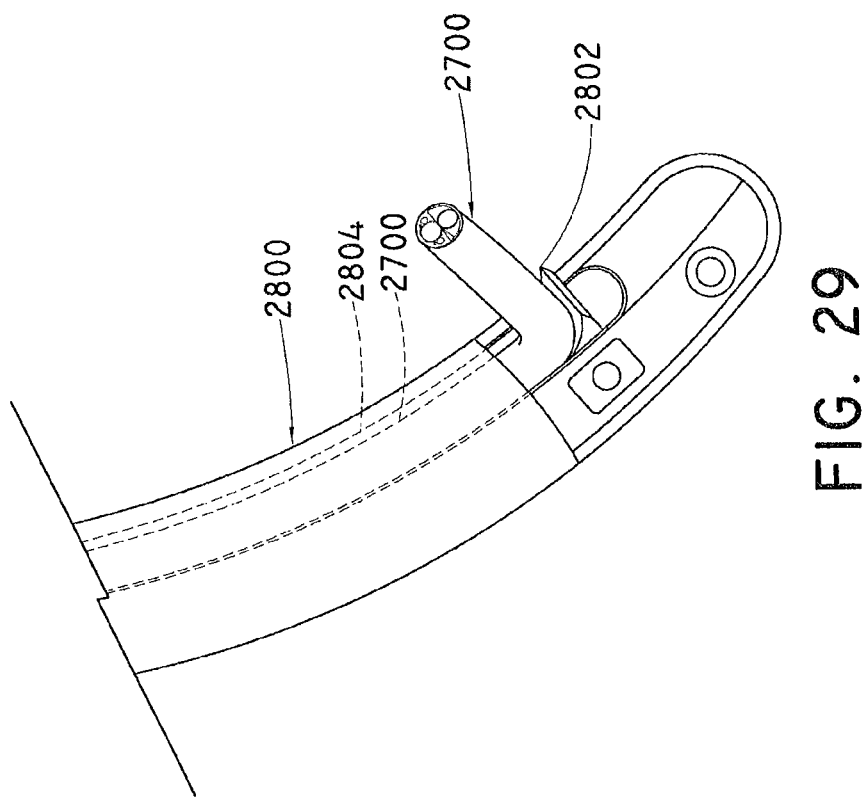

SPACE-OPTIMIZED VISUALIZATION CATHETER WITH CAMERA TRAIN HOLDER IN A CATHETER WITH OFF-CENTERED LUMENS

CROSS-REFERENCE TO RELATED APPLICATION

This application claims the benefit of U.S. Provisional Application No. 61/581,394, filed Dec. 29, 2011. The contents of U.S. Provisional Application No. 61/581,394 are incorporated by reference in their entirety.

TECHNICAL FIELD

The present invention relates to medical devices and more specifically, visualization catheters.

BACKGROUND

Endoscopes are routinely used to provide direct visualization to medical personnel while performing medical procedures. To enable medical personnel to reach smaller portions of the anatomy, medical personnel often use a "baby scope." Baby scopes are visualization catheters that are configured for disposition through a working channel of an endoscope. However, known baby scopes are difficult to use and the working channel, fluid lumen, and light lumens disposed therein are too small and/or too few in number to efficiently perform many medical procedures.

The size of the outer diameter of the baby scope is generally fixed at 3.5 mm. The internal working space available for working channel lumens, fluid lumens, and light lumens are dictated by numerous factors. Such factors, which alone or in combination contribute to a large outer diameter or reduced interior work space, include, but are not limited to, the thickness of the catheter wall, the amount and size of cabling, lighting equipment, working channel lumens disposed therein, the image gathering equipment (such as charge coupled device ("CCD") technology) utilized to gather an image, as well as the devices necessary to maintain the proper position of each of the devices disposed within the baby scope. In other words, in the case of a CCD-equipped baby scope, the CCD sensor must be held in proper position along with all the cables, power supplies, and other equipment necessary to enable the CCD sensor to capture an image. The extraneous materials necessary to properly position the camera equipment such that it can gather an image utilize valuable space within a baby scope.

Present baby scopes suffer from additional drawbacks in addition to their minimal internal working space. These drawbacks include, but are not limited to, poor image quality and ability to capture an image from, for example, the use of bulky camera equipment.

BRIEF SUMMARY

In a first aspect, a visualization catheter is provided. The visualization catheter includes a catheter having a proximal catheter portion; a distal catheter portion; and a working channel lumen extending through the proximal catheter portion and the distal catheter portion. The catheter also has a cabling lumen extending through the proximal catheter portion and the distal catheter portion and adjacent to the working channel lumen; and a notch disposed into an inner surface of the distal catheter portion. The notch is off-centered from the cabling lumen and connected to the cabling lumen. In addition, the visualization catheter includes a camera train holder that has a proximal camera train holder portion configured to receive a visualization sensor; and a distal camera train holder portion configured to receive a lens stack. The camera train holder is disposed within the notch of the catheter.

In a second aspect, a second visualization catheter is provided. The second visualization catheter includes a catheter that has a proximal catheter portion; a distal catheter portion having a taper; a working channel lumen extending through the proximal catheter portion and the distal catheter portion, wherein the working channel exits at a side of the catheter; a cabling lumen extending through the proximal catheter portion and the distal catheter portion and adjacent to the working channel lumen; and a notch disposed into an inner surface of the distal catheter portion. The notch is off-centered from the cabling lumen and connected to the cabling lumen. In addition, the second visualization catheter includes a camera train holder that has a proximal camera train holder portion configured to receive a visualization sensor; and a distal camera train holder portion configured to receive a lens stack. The camera train holder is disposed within the notch of the catheter.

In a third aspect, a method of manufacturing a visualization catheter is provided. The method of manufacturing includes extruding a catheter that has a proximal catheter portion; a distal catheter portion; a working channel lumen extending through the proximal catheter portion and the distal catheter portion; and a cabling lumen extending through the proximal catheter portion and the distal catheter portion and adjacent to the working channel lumen. The method also includes removing a notch from an inner surface of the distal catheter portion. The notch is off-centered from the cabling lumen and connected to the cabling lumen. In addition, the method includes providing a camera train holder that has a proximal camera train holder portion configured to receive a visualization sensor, and a distal camera train holder portion configured to receive a lens stack. The method further includes coupling the camera train holder into the notch of the catheter.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

FIG. 2A illustrates a perspective view of a first embodiment of a space-optimized visualization catheter;

FIG. 7 illustrates a perspective view of an illustrative camera train holder of the space-optimized visualization catheter illustrated in FIG. 2A;

FIG. 8 illustrates a front view of the proximal portion of the space-optimized visualization catheter illustrated in FIG. 2A;

FIG. 9 illustrates a back view of the proximal portion of that which is illustrated in FIG. 8;

FIG. 10 illustrates a cross-sectional view along the line A-A illustrated in FIG. 4;

FIG. 11 illustrates a cross-sectional view along the line B-B illustrated in FIG. 4;

FIG. 12 illustrates a perspective view of a second embodiment of a space-optimized visualization catheter;

FIG. 13 illustrates a perspective view of a second embodiment of a camera train holder for use with the space-optimized visualization catheter illustrated in FIG. 12;

FIG. 14 illustrates a back view of the camera train holder illustrated in FIG. 13;

FIG. 15 illustrates a perspective view of another embodiment of a space-optimized visualization catheter;

FIG. 16 illustrates a perspective view of another embodiment of a camera train holder for use with the space-optimized visualization catheter illustrated in FIG. 15;

FIG. 17 illustrates a cross-sectional perspective view of the camera train holder illustrated in FIG. 16;

FIG. 17A illustrates a perspective view of a lens stack configured to have two cross-sectional profiles.

FIG. 20 illustrates a schematic view of the space-optimized visualization catheter illustrated in FIG. 18;

FIG. 20A illustrates a perspective view of an alternate embodiment of a space-optimized visualization catheter;

FIG. 20B illustrates a cross-sectional perspective view of the space-optimized visualization catheter illustrated in FIG. 20A;

FIG. 21 illustrates a perspective view of another embodiment of a space-optimized visualization catheter;

FIG. 22 illustrates a cross-sectional perspective view of the space-optimized visualization catheter illustrated in FIG. 21;

FIG. 27 illustrates a perspective view of another embodiment of a space-optimized visualization catheter;

FIG. 28 illustrates a schematic view of the space-optimized visualization catheter illustrated in FIG. 27; and FIG. 29 illustrates the space-optimized visualization catheter illustrated in FIG. 27 in use.

DETAILED DESCRIPTION OF PRESENTLY PREFERRED EMBODIMENTS

Figure 1B:
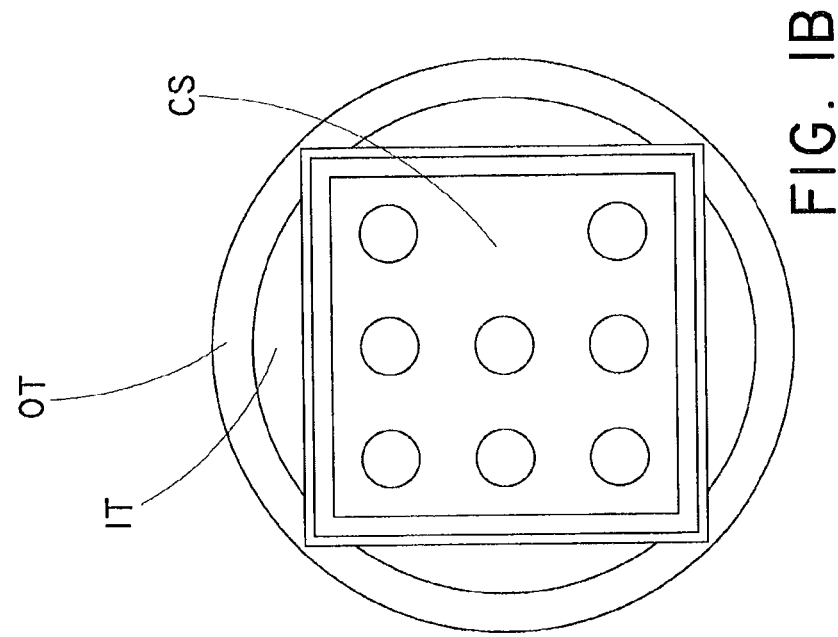
FIG. 1B illustrates a rear view of the conventional CMOS sensor holder illustrated in FIG. 1A.

The exemplary embodiments illustrated provide the discovery of methods and apparatuses for visualization catheters that utilize a visualization sensor, including but not limited to, complimentary metal-oxide-semi-conductor ("CMOS") sensor technology integrated into a CMOS camera train holder system that may be a stand-alone component for use with a visualization catheter, such as a baby endoscope, or may be fabricated/extruded as a part of the catheter itself. Embodiments of apparatuses, methods, and equivalents thereto provide many benefits, including but not limited to, better direct visual feedback to the medical personnel performing the procedure while providing a similarly-sized outer diameter visualization catheter device having more space therein for additional lumens and equipment than present baby scopes or by utilizing a smaller outer diameter visualization catheter.

Diseases and conditions contemplated for treatment include, but are not limited to, those involving the gastrointestinal region, esophageal region, duodenum region, biliary region, colonic region, urological region (e.g., kidney, bladder, urethra), ear, nose, and throat (e.g., nasal/sinus) region, bronchial region, as well as any other bodily region or field benefiting from direct visualization of a target site for treatment or diagnosis.

The present invention is not limited to those embodiments illustrated herein, but rather, the disclosure includes all equivalents including those of different shapes, sizes, and configurations, including but not limited to, other types of visualization catheters and component parts. The devices and methods may be used in any field benefiting from a visualization catheter or parts used in conjunction with visualization catheters. Additionally, the devices and methods are not limited to being used with human beings; others are contemplated, including but not limited to, animals.

Unless otherwise defined, all technical and scientific terms used herein have the same meaning as commonly understood by one of ordinary skill in the art. In case of conflict, the present document, including definitions, will control. Preferred methods and materials are illustrated below, although apparatuses, methods, and materials similar or equivalent to those illustrated herein may be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

Figure 1A:
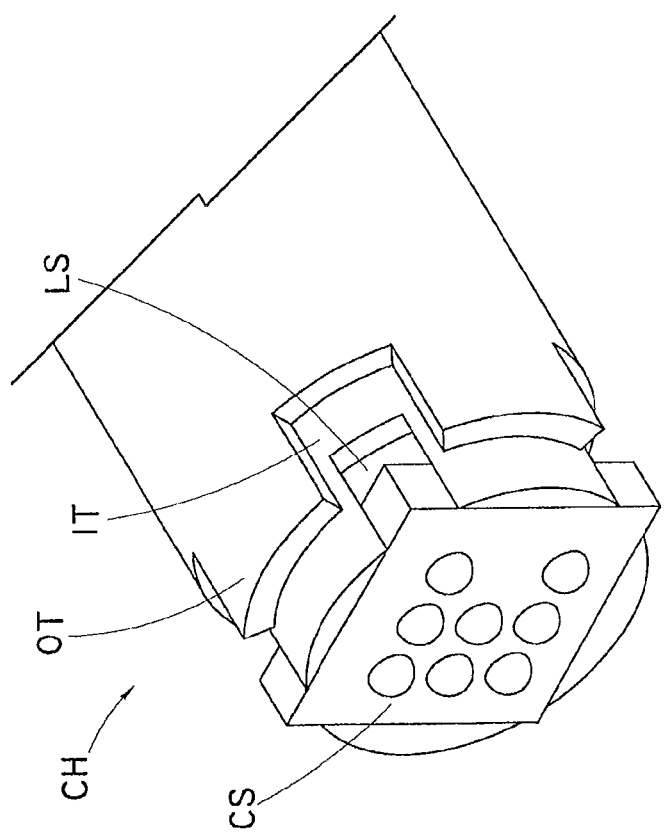
FIG. 1A illustrates a perspective view of a conventional CMOS sensor holder.
Figure 1C:
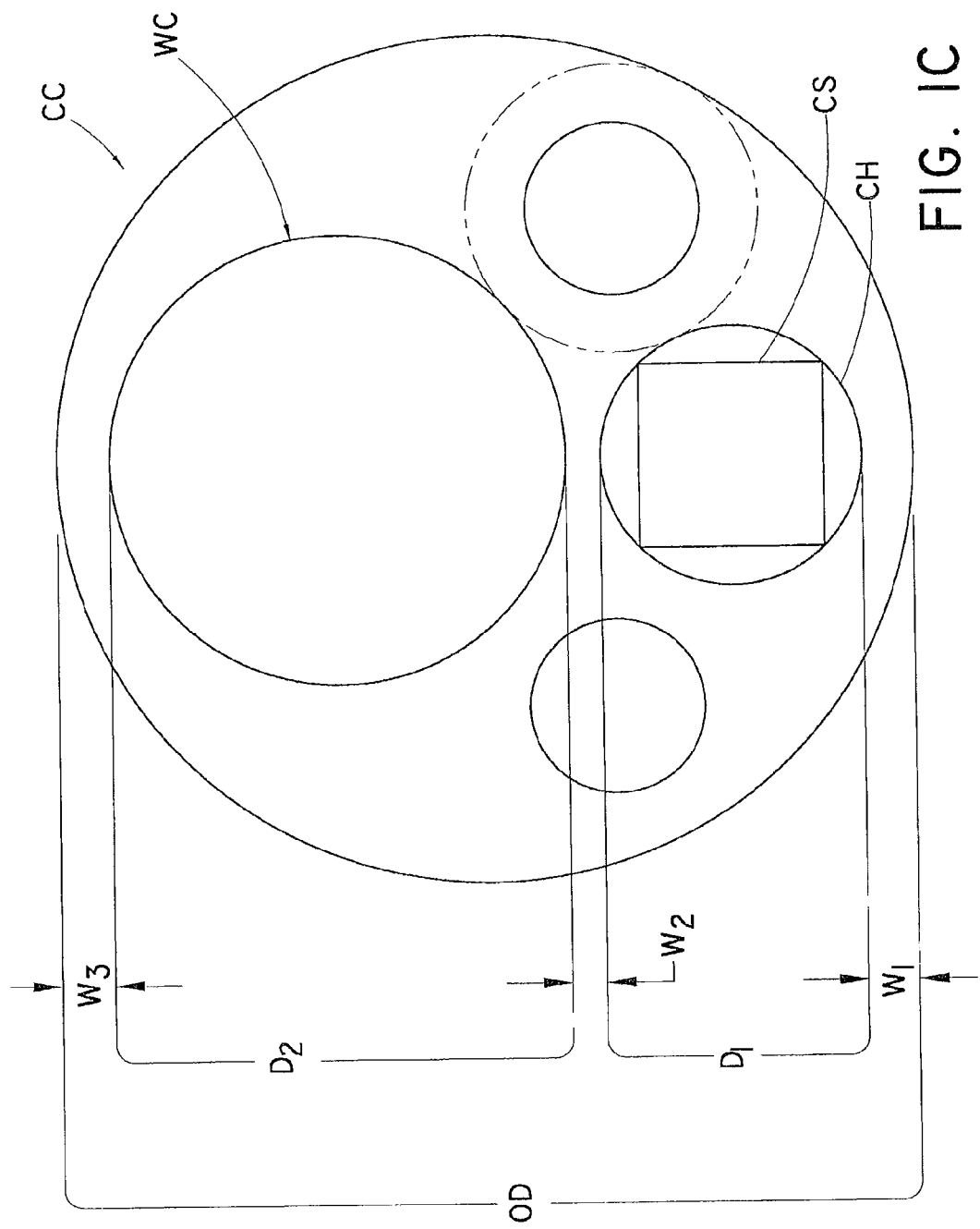
FIG. 1C illustrates a schematic front view of a conventional catheter utilizing the conventional holder illustrated in FIG. 1A.

FIG. 1A illustrates a perspective view of conventional CMOS sensor holder CH, FIG. 1B illustrates a rear view of conventional CMOS sensor holder CH illustrated in FIG. 1A, and FIG. 1C illustrates a schematic front view of conventional catheter CC utilizing conventional CMOS sensor holder CH illustrated in FIG. 1A. Referring to FIGS. 1A-1C, conventional holder CH is 2.6 mm in diameter and is composed of two pieces of stainless steel tubing: inner tubing IT and outer tubing OT. Inner piece of tubing IT is used to secure CMOS sensor CS to a plane that is perpendicular to the optical axis of the telecentric lens stack LS. Outer piece of tubing OT is used to hold lens stack LS and can move parallel to the optical axis to fine tune the depth of field. Even though conventional holder CH illustrated in FIGS. 1A-1C is configured to fit the diagonal of the square CMOS image sensor CS, the design does not optimize the space that drives the outer diameter of conventional holder CH and conventional catheter CC. This space is composed of working channel WC, conventional CMOS sensor holder CH, and the three webs of the catheter as illustrated in FIG. 1C.

Referring to FIG. 1C, outer diameter OD of conventional catheter CC is the sum of D1+D2+W1+W2+W3, where D1 is the diameter of conventional holder CH; D2 is the diameter of working channel WC; and W1, W2, and W3 are each conventional catheter CC webbing. If outer diameter OD of conventional catheter CC is fixed and cannot be larger than 3.5 mm, CMOS sensor CS has a fixed size of 1.8 mm×1.8 mm square, and working channel WC must be maximized, then the sensor holder must be configured to be as small as possible and the webs of the devices must be as thin as possible.

A more detailed description of the embodiments will now be given with reference to FIGS. 2A-29. Throughout the disclosure, like reference numerals and letters refer to like elements. The present disclosure is not limited to the embodiments illustrated; to the contrary, the present disclosure specifically contemplates other embodiments not illustrated but intended to be included in the claims.

Figure 2B:
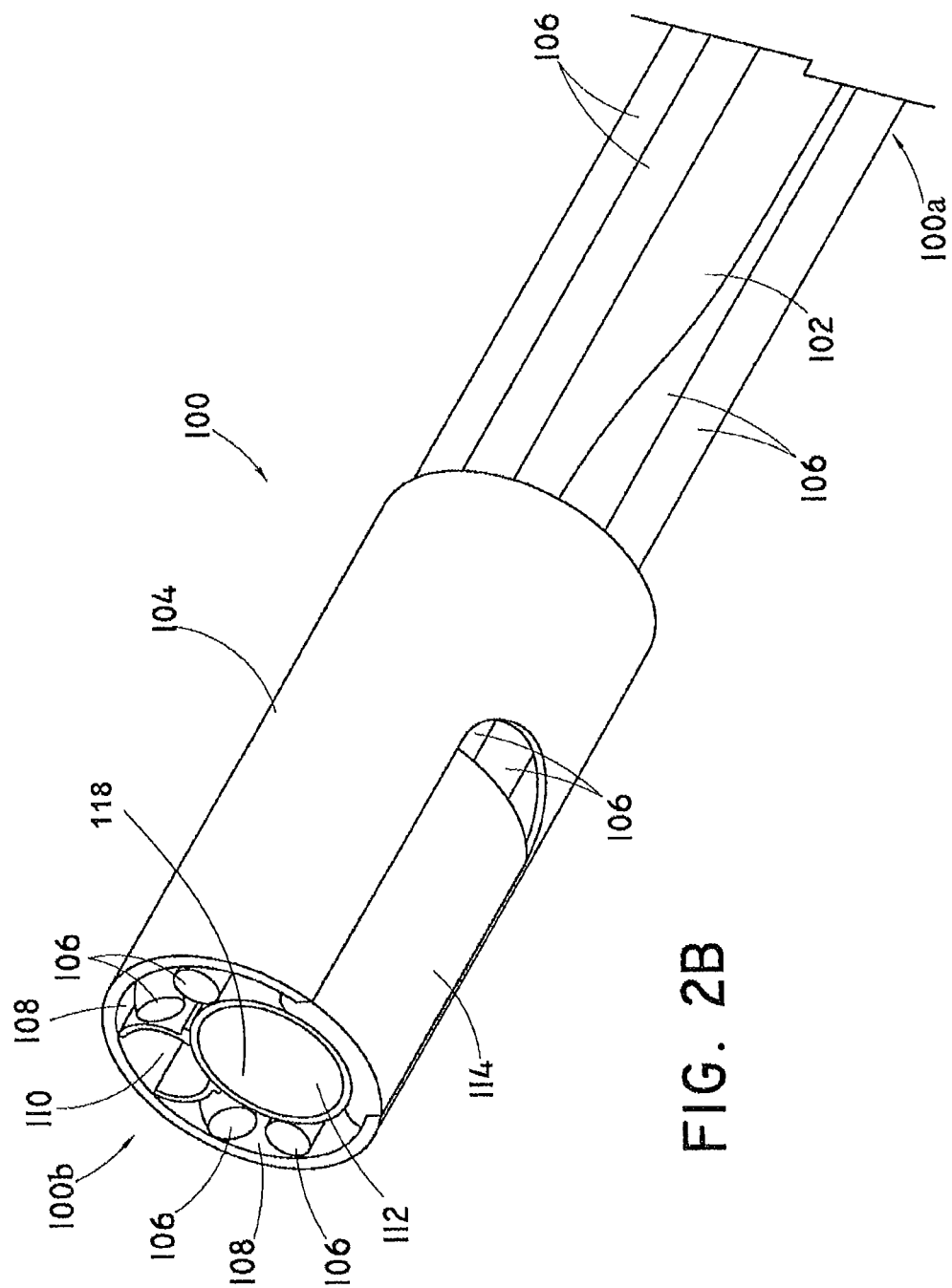
FIG. 2B illustrates a bottom perspective view of the space-optimized visualization catheter illustrated in FIG. 2A.

FIG. 2A illustrates a perspective view of space-optimized visualization catheter 100, and FIG. 2B illustrates a bottom perspective view of space-optimized visualization catheter 100. Space-optimized visualization catheter 100 has proximal portion 100a and distal portion 100b. Space-optimized visualization catheter 100 and equivalents thereto overcome the disadvantages with conventional catheter CC and conventional holders CH, such as those illustrated in FIGS. 1A-1C.

Referring to FIGS. 2A-2B, space-optimized visualization catheter 100 includes outer sheath 104. Disposed within outer sheath 104 are camera train holder 114, inner catheter 102, outer sheath 104, illumination fibers 106, flushing voids 108, working channel 110, and image capturing surface 112 of lens stack 118. For illustrative purposes only, outer sheath 104, illumination fibers 106, and inner catheter 102 are illustrated truncated and generally would extend proximally to a control handle (not shown) of the device.

Space-optimized visualization catheter 100 and equivalents thereto solve and provide solutions to numerous challenges facing known baby scopes. For example, space-optimized visualization catheter 100 and equivalents thereto solve the problem of constraints of space, which arise from the need to limit the overall size (e.g., the outer diameter) of the transverse cross-section of scopes. With the overall cross-section limited, the available space should be judiciously allocated to elements that perform important functions.

Space-optimized visualization catheter 100 and equivalents thereto manage and address at least four important scope functions vying for space: image capture, working channel, flushing, and illumination. Generally, the functions of image capture and the working channel together drive the overall diameter of the cross-section thereby leaving the flushing and illumination functions competing for any space that remains.

Space-optimized visualization catheter 100 and equivalents thereto also provide a solution to numerous secondary challenges facing known baby scopes. For example, space-optimized visualization catheter 100 and equivalents thereto solve the problems of ease of construction, component cost, optimization of materials for function, sealing of opto-electronic components and connections against moisture and light, ability to properly align the lens system to the sensor image plane, ability to focus images onto the sensor image plane, and ability to direct the light emanating from the illumination system.

Figure 3:
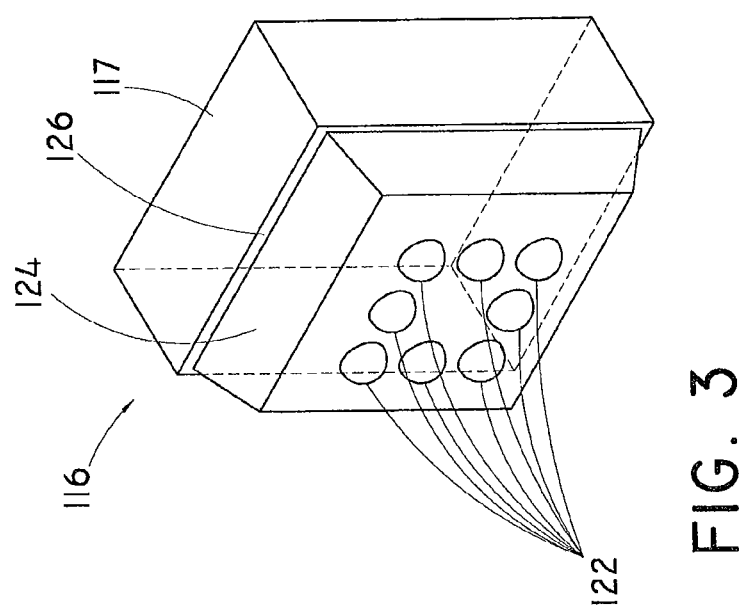
FIG. 3 illustrates a perspective view of a CMOS sensor of the space-optimized visualization catheter illustrated in FIG. 2A.

FIG. 3 illustrates a perspective view of CMOS sensor 116 of space-optimized visualization catheter 100 illustrated in FIG. 2A. Referring to FIGS. 2A-3, disposed within outer sheath 104 is camera train holder 114 which houses CMOS sensor 116 in proper relation to lens stack 118. CMOS sensor 116 is a visualization sensor and preferably is approximately the shape of a square tile although other shapes and configurations are contemplated. One side of CMOS sensor 116 is configured to receive an image and includes a thickness of transparent glass (cover glass) 117. The other side of CMOS sensor 116 includes an integrated circuit (IC die) 124 and is configured for electrical connection with raised solder balls 122. Image plane 126 lies within CMOS sensor 116 at a surface that forms the junction between IC die 124 and cover glass 117.

Figure 4:
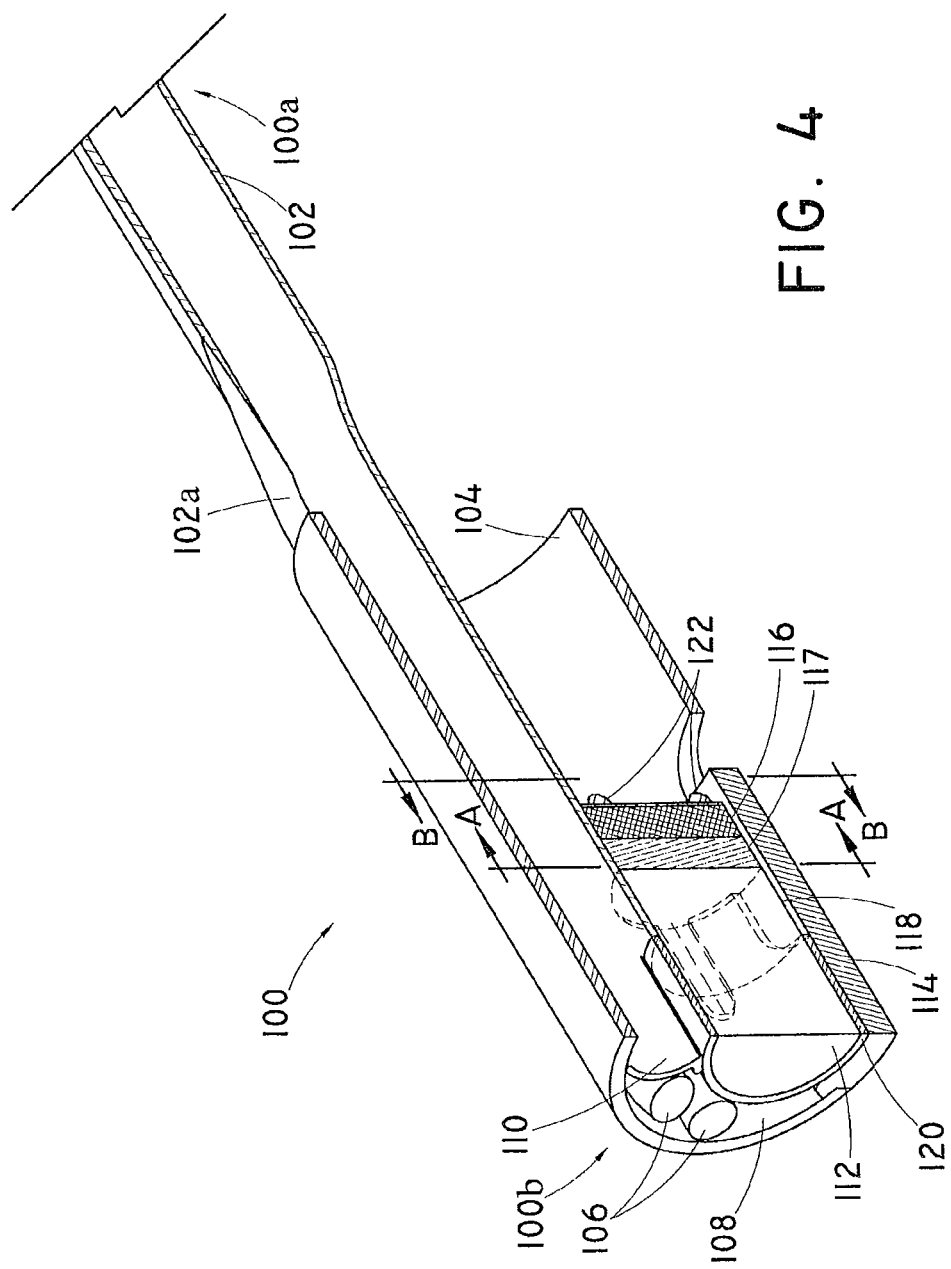
FIG. 4 illustrates a cross-sectional perspective view of the space-optimized visualization catheter illustrated in FIG. 2A.
Figure 5:
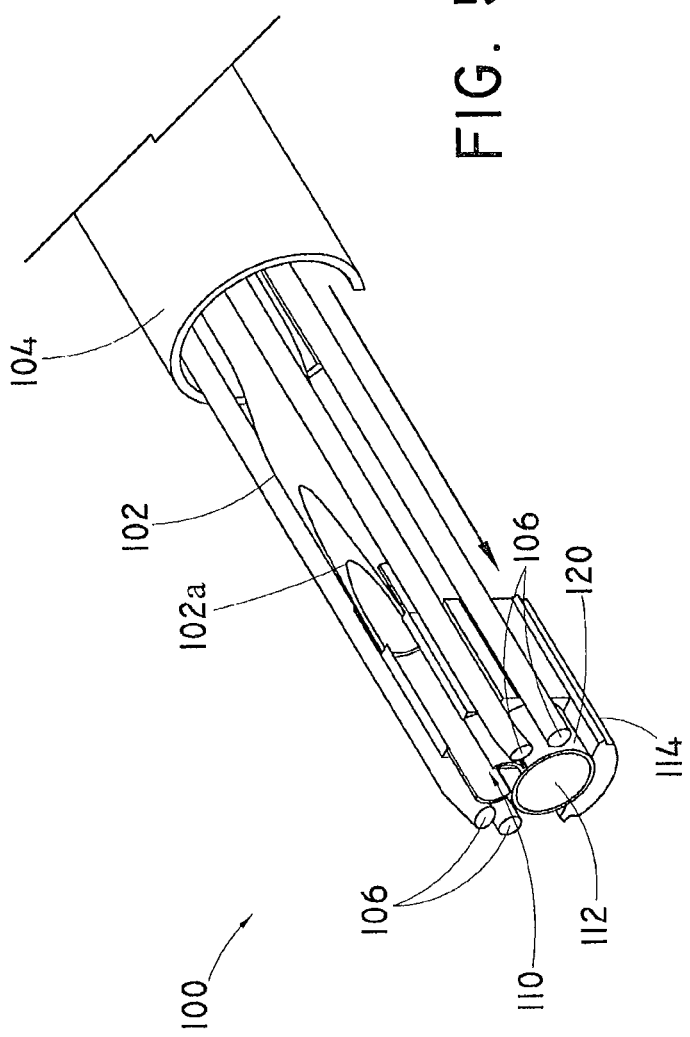
FIG. 5 illustrates a partially stripped perspective view of the space-optimized visualization catheter illustrated in FIG. 2A.

FIG. 4 illustrates a cross-sectional perspective view of space-optimized visualization catheter 100 illustrated in FIG. 2A, and FIG. 5 illustrates a partially stripped perspective view of space-optimized visualization catheter 100 illustrated in FIG. 2A. Referring to FIGS. 4-5, for illustrative purposes only, outer sheath 104, illumination fibers 106, and inner catheter 102 are illustrated truncated and generally would extend proximally to a control handle (not shown) of the device.

Referring to FIGS. 2A-5, lens stack 118 is composed of one or more lens elements, including but not limited to, glass, polymer, or combination thereof. It is contemplated that lens stack 118 may further include one or more coatings, filters, apertures, or combinations thereof. Lens stack 118 is housed within lens holder 120. Lens holder 120 is preferably a thin-walled cylindrical element configured for holding lens stack 118. It is preferred that lens holder 120 be made from a stainless steel hypodermic tube, although other materials and configurations are contemplated. Not illustrated is the electrical cabling assembly that would generally extend along the length of space-optimized visualization catheter 100 and connect to solder balls 122 of CMOS sensor 116.

Camera train holder 114 along with lens holder 120 together house and hold lens stack 118 and CMOS sensor 116 so as to orient image plane 126 perpendicular and centered with respect to the central axis of lens stack 118. Camera train holder 114 along with lens holder 120 together also shield the periphery of CMOS sensor 116 from stray light to reduce or eliminate imaging artifact/noise. Accordingly, any light falling upon the sides of cover glass 117 or IC die 124 are restricted so that only the light passing through lens stack 118 reaches image plane 126.

Camera train holder 114 along with lens holder 120 together also permit the proximal aspect of CMOS sensor 116 comprising solder balls 122 to have electrical connections made thereupon and to be sealed from both light and fluid. This is achieved, for example, by filling the square pocket in camera train holder 114 proximal to CMOS sensor 116 with potting material, such as but not limited to, epoxy or silicone, thereby insulating the electrical cable(s) (not shown) to emerge therefrom. Accordingly, camera train holder 114, lens stack 118, and CMOS sensor 116 with electrical cable(s) (not shown) are sealed together forming a moisture-impervious and light-impervious (except through the lenses) camera module that may improve the image capture function. With inner catheter 102 joined thereto, camera train holder 114 also performs the function of providing an integrated working channel 110.

One benefit, among many, of the manner in which lens stack 118 is housed within camera train holder 114 and lens holder 120 is that it permits lens stack 118 to be controllably moved closer to and further from image plane 126 for focusing purposes. After being focused, the position of lens stack 118 and image plane 126 are thereby fixed by using, for example, an adhesive or other material or means. Permitting the distal aspect of lens stack 118 to be sealed to camera train holder 114 prevents fluid encroachment into the interior aspects.

Figure 6:
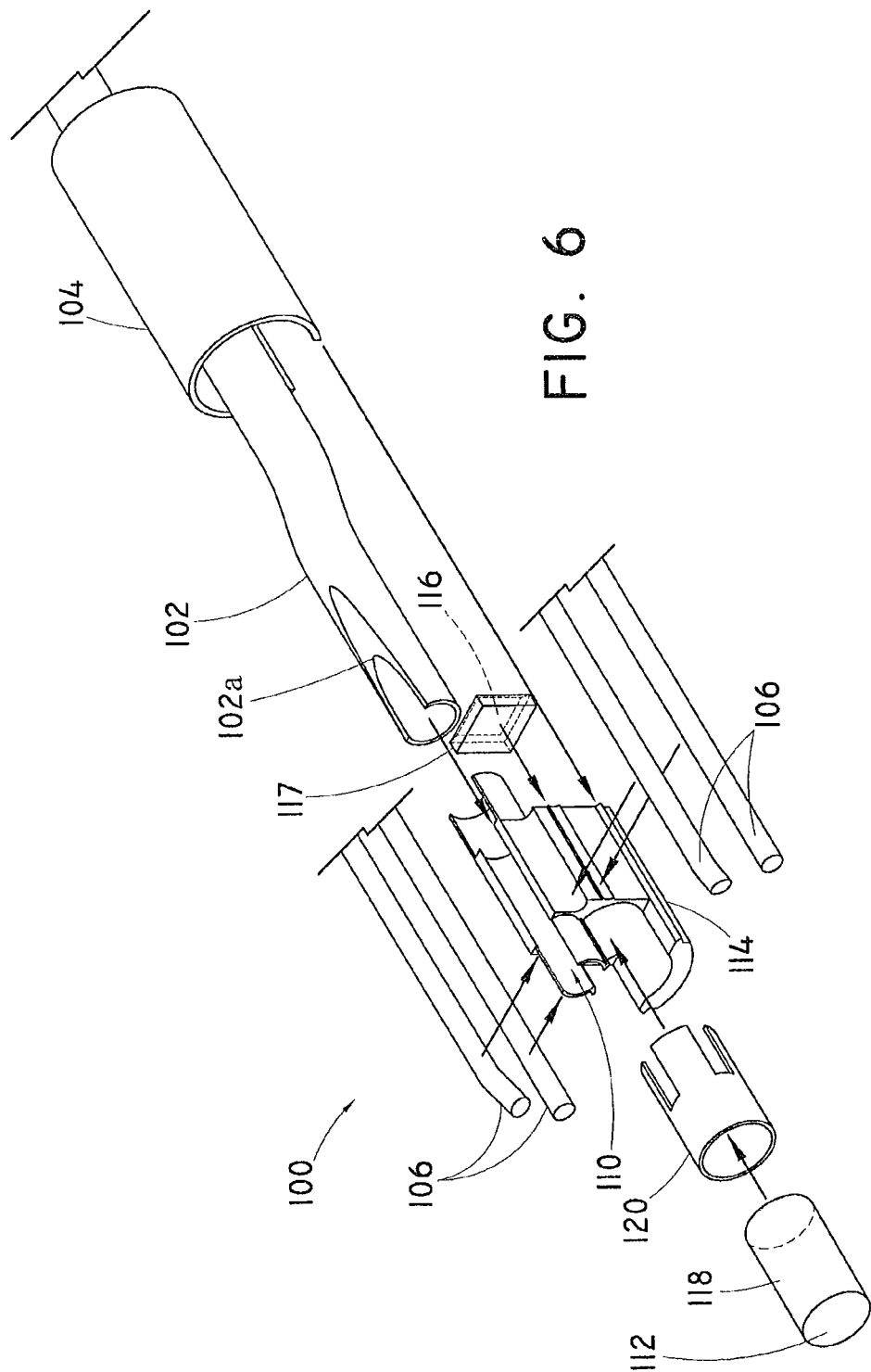
FIG. 6 illustrates an exploded perspective view of the space-optimized visualization catheter illustrated in FIG. 2A.

FIG. 6 illustrates an exploded perspective view of space-optimized visualization catheter 100 illustrated in FIG. 2A, and FIG. 7 illustrates a perspective view of illustrative camera train holder 114 of space-optimized visualization catheter 100 illustrated in FIG. 2A. Referring to FIGS. 6-7, for illustrative purposes only, outer sheath 104, illumination fibers 106, and inner catheter 102 are illustrated truncated and generally would extend proximally to a control handle (not shown) of the device.

Referring to FIGS. 2A-7, atop camera train holder 114 are cylindrical wall features extending upwards to form the distal-most portion of working channel 110 within the overall assembly. These walls do not form a complete cylinder, but are instead truncated so that they do not extend beyond the surface formed by the inner diameter of outer sheath 104. Thus, the proximal aspect of working channel 110 formed by the walls of camera train holder 114 is configured to receive the distal end of inner catheter 102 such that the inner diameter of inner catheter 102 is contiguous with the inner diameter of working channel 110 formed by the walls. As such, a portion of the diameter of the device equal to the wall section left out is saved. Thus, a single working channel 110 is formed from camera train holder 114 and inner catheter 102 that has a smooth, contiguous inner surface.

Inner catheter 102 and equivalents thereto may be affixed to camera train holder 114 by, for example, an adhesive or welding. In the region where inner catheter 102 and camera train holder 114 are joined, inner catheter 102 is co-axial with working channel 110 formed by the wall features of camera train holder 114.

Proximal to where inner catheter 102 and camera train holder 114 join, a central longitudinal axis of inner catheter 102 is displaced or offset from a central longitudinal axis of work channel 110. In one example, proximal to the where inner catheter 102 and camera train holder 114 join, the central axis of inner catheter 102 is positioned at a central axis of the entire assembly. In addition, as best illustrated in FIG. 7, a distal portion of an outer wall 102a of inner catheter 102 includes groove portion 102b that provides a transition from an outer surface 102c of outer wall 102a to a gap or opening 102d in the outer wall 102a. The gap or opening 102d extends from a proximal portion of groove portion 102b to a distal end of the catheter 102. In addition, groove portion 102b distally extends and transitions to upper surfaces 102e. Upper surfaces 102e is smooth or substantially smooth. In addition, upper surface 102e is flush with upper surfaces 114c of camera train holder 114. As shown in FIGS. 4 and 5, inner catheter 102 joins with camera train holder 114 so that a distance from upper surfaces 102e and 114c to a bottom-most portion of camera train holder 114 does not exceed or extend an inner diameter of outer sheath 104.

At a more proximal location, where inner catheter 102 is displaced into a more central position, its walls may be left intact without interfering with the wall of outer sheath 104.

Inner catheter 102 and equivalents thereto may be constructed from any flexible material but are preferably constructed from a low-friction polymer such as polytetrafluoroethylene ("PTFE") or fluorinated ethylene propylene ("FEP"). Inner catheter 102 and equivalents thereto may also be reinforced over all or a part of the length with a braid and/or coil of metal or other relatively strong/stiff material.

The form of outer sheath 104 is that of a cylindrical tube. Outer sheath 104 and equivalents thereto may be made from a variety of materials but are preferably constructed from a flexible polymer reinforced with a braid and/or coil of metal or other relatively strong/stiff material to provide a flexible tube that is capable of making tight bends without collapsing or kinking.

The proximal ends of the electrical cable(s) (not shown) to connect with CMOS sensor 116 and inner catheter 102 may be loaded into the distal end of the outer sheath 104 and pulled therethrough to bring camera train holder 114 in close proximity to the distal end of outer sheath 104. Camera train holder 114 assembles to outer sheath 104 in such a way as to allow camera train holder 114 to form part of the outer cylindrical surface of the assembly where a portion of the lower wall of camera train holder 114 has been removed (as is best illustrated in FIG. 2B).

FIG. 8 illustrates a front view of the proximal portion of space-optimized visualization catheter 100 illustrated in FIG. 2A, FIG. 9 illustrates a back view of the proximal portion of that which is illustrated in FIG. 8, FIG. 10 illustrates a cross-sectional view along the line A-A illustrated in FIG. 4, and FIG. 11 illustrates a cross-sectional view along the line B-B illustrated in FIG. 4. Referring to FIGS. 2A-11, and more particularly, FIGS. 2B, 7, and 8-11, one advantage, among many, of space-optimized visualization catheter 100 and equivalents thereto is to gain a reduction in diameter of the device equal to the wall left out. Receiving groove 114a has been formed into the lower left and right aspects of camera train holder 114 to receive the edges of outer sheath 104 where the lower wall of outer sheath 104 has been removed. Accordingly, receiving groove 114a is configured for coupling to outer sheath 104. This may facilitate joining with adhesives and/or welding, but other configurations and joining methods may be used. Preferably the method would include laser welding.

The assembly comprising the combination of camera train holder 114 joined to outer sheath 104, in the region of the distal tip, camera train holder 114 only occludes a portion of the space defined by the inner diameter of outer sheath 104. Accordingly, on either side of camera train holder 114 there is a void formed between the inner surface of outer sheath 104 and the outer surface of camera train holder 114. This space may be utilized for a variety of purposes.

For example, in the embodiment illustrated here, the void formed between the inner surface of outer sheath 104 and the outer surface of camera train holder 114 is utilized to provide both illumination grooves 114b and flushing 108 capability. There is ample space to accommodate one or more optical light fibers 106 (or bundles of fibers) for light delivery. Accordingly, as illustrated in this embodiment, four such light fibers 106 are illustrated, although more or less are contemplated. Preferably, light fibers 106 may be adhered to illumination groove 114b of camera train holder 114 prior to camera train holder 114 being inserted through and affixed to outer sheath 104 (as illustrated in FIG. 5). However, other orders of assembly are contemplated, and fibers 106 need not necessarily be adhered to the assembly at all.

Still referring to FIGS. 2A-11, optical fibers 106 are positioned within the areas of the cross-section that most readily accommodate them, such as illumination grooves 114b, which include shallow radiused features on the lateral and upper aspects of the outer surface of camera train holder 114, to assist in properly positioning lighting means for lighting a target site, such as optical fibers 106 and to provide surfaces to bond them thereto, using for example, an adhesive. Light fibers 106 project light cones 106a therefrom, as illustrated in FIG. 2A. The remaining space around optical fibers 106 provides a flushing means for fluid flow 108. Accordingly, fluid may be forced to flow within the interior void 108 of outer sheath 104, in and around the spaces about optical fibers 106 (as best illustrated in FIGS. 8-9) and the outer surface of camera train holder 114, and exit out from distal portion 100b of space-optimized catheter 100. In addition, the transverse cross-sectional size of the interior void 108 may vary. For example, the size of interior void 108 is one size where camera train holder 114 does not form part of the interior of space-optimized visualization catheter 100 and another size where camera train holder 114 does form part of the interior of space-optimized visualization catheter 100. The size of interior void 108 where camera train holder 114 does not form part of the interior is larger than the size of interior void 108 where camera train holder 114 does form part of the interior.

One method of assembling space-optimized visualization catheter 100, includes but is not limited to, providing outer sheath 104; providing inner catheter 102; providing camera train holder 114; coupling a visualization sensor, such as CMOS sensor 116 and lens stack 118 to camera train holder 114; coupling inner catheter 102 to a portion of camera train holder 114 thereby forming working channel 110; inserting camera train holder 114 and inner catheter 110 into a lumen of outer sheath 104 such that camera train holder 114 forms a boundary of an outer surface of outer sheath 104. Additionally, cables may be coupled to CMOS sensor 116 before camera train holder 114 and inner catheter 110 are inserted into outer sheath 104.

There are numerous advantages to space-optimized visualization catheter 100 and equivalents thereto. For example, a primary challenge with present baby scopes is to limit the overall size of the transverse cross-section of the device, where the space requirements for the functions of image capture and working channel play an important role. Image quality relates very strongly to resolution (pixel count), which relates very strongly to sensor size. Also, working channel utility relates very strongly to channel size, as that determines which wireguides and other devices may be passed therethrough. Thus, the larger the sensor and working channel may be, the more useful the catheter may be. Nevertheless, the overall size of the catheter is also a limiting factor when, for example, the catheter is to be placed in a narrowly restricted body lumen and/or through a channel within a larger instrument, such as a duodenoscope. Thus, optimization of a design with respect to these factors (sensor size, channel size, overall size) is important. Space-optimized visualization catheter 100 and equivalents thereto address these challenges in significant, discovered ways.

For example, camera train holder 114 forms part of the outer cylindrical surface of space-optimized visualization catheter 100 together with outer sheath 104. One advantage of this is that it permits the square pocket that is configured to house CMOS sensor 116 (at best illustrated in FIGS. 8-11) to be moved much closer to the outer cylindrical surface of space-optimized visualization catheter 100. Accordingly, the material between the outermost edges of the square pocket can be relatively thin if the material utilized is relatively rigid and/or strong.

For space-optimized visualization catheter 100 and equivalents thereto, materials for outer sheath 104 construction are typically and ideally relatively soft and flexible in comparison to materials that may be used to fabricate camera train holder 114, such as metals or high performance polymers for injection molding. Thus, by forming camera train holder 114 from a relatively stronger and/or more rigid material than outer sheath 104, space may be gained in the cross-section by moving CMOS sensor 116 closer to the outer cylindrical surface of space-optimized visualization catheter 100.

Another advantage, for example, of space-optimized visualization catheter 100 and equivalents thereto is that working channel 110 is formed primarily from a separate inner catheter 102 that is distinct from outer sheath 104. One advantage, among many, is that such a configuration allows for optimization of materials for the purpose. In other words, the materials from which inner catheter 102 may be manufactured may include a low-friction polymer; other materials are contemplated. Thus, because working channel 110 is not integral to outer sheath 104, the material from which the assembly may be made is not in conflict with one another. Thus, space-optimized visualization catheter 100 and equivalents thereto does not require a) a compromise in performance of one or both of the functions, or b) a more complex construction, e.g., such as a reinforced flexible outer sheath with an integral second lumen for a working channel that is lined with a thin membrane of low-friction polymer—such a construct may be more costly to produce and may also require more space.

Another advantage, for example, of space-optimized visualization catheter 100 and equivalents thereto is that distal working channel 110 is formed from cylindrical walls integral to camera train holder 114 that are joined to inner catheter 102. One advantage, among many, is that such a construction permits the location of working channel 110 within the cross-section to be controlled and optimized for space at a location along the length of space-optimized visualization catheter 100 where it is generally most important, i.e., at the distal end where a camera module (sensor & lens) must also be accommodated. This is primarily enabled via the utilization of relatively stiff and/or strong materials of construction for camera train holder 114.

The distal-most aspect of working channel 110 is configured from the relatively rigid material of camera train holder 114. This permits the location of working channel 110 to be moved further towards the outside surface of the overall assembly than would be possible otherwise. Specifically, the material of camera train holder 114 is strong/stiff enough to permit forming working channel 110 from walls that do not form a complete cylinder, but instead are truncated so that they do not extend beyond the surface formed by the inner diameter of outer sheath 104. Second, the relatively rigid material of camera train holder 114 permits the wall between the lumen of working channel 110 and the sensor/lens assembly to be relatively thin, which reduces the size of the overall assembly.

Another advantage, for example, of space-optimized visualization catheter 100 and equivalents thereto is that camera train holder 114 includes only minimal features for locating/fixing the positions of illumination fibers 106 within the assembly, which leaves more space for flushing 108. By contrast, if a catheter with dedicated illumination channels were provided, the walls forming those channels may consume important space. Instead, illumination fibers 106 illustrated are permitted to reside in spaces where they are accommodated and partially positioned by the outer surface of camera train holder 114 on one side/aspect (illumination grooves 114b) and outer sheath 104 on another. Beyond that, only minimal features are included to further stabilize the positions.

Another advantage, for example, of space-optimized visualization catheter 100 and equivalents thereto is that the distal-most portion of camera train holder 114 includes void 114b (such as a notch, groove, or recess) between the walls forming the distal end of working channel 110 and the lower aspect of camera train holder 114 that forms the outer surface of space-optimized visualization catheter 100. Void 114b provides a space into which the distal portion of illumination fibers 106 may be directed in order to better direct the light emanating therefrom to the target site without constructing a separate chamber or lumen to house light fibers 106 (which may add bulk and reduce space). This provides more versatility for optimization of lighting than if the perimeter of camera train holder 114 were constant from the region of CMOS sensor 116 to the distal face of camera train holder 114.

Another advantage, for example, of space-optimized visualization catheter 100 and equivalents thereto is that the capability for flushing is accomplished "in the negative." In other words, there are no included features intended solely or specifically to guide fluid for flushing, but rather, flushing void 108 is bound by the inner surface of outer sheath 104 and the outer surface of camera train holder 114. Camera train holder 114 is configured to facilitate sealing of the opto-electric components so that the entire interior of space-optimized visualization catheter 100 may be used for fluid flow 108. One advantage to this construction is that it maximizes the area in the cross section that is available for fluid flow in the region where that is most restricted, i.e., in the region of the camera module.

Also, space-optimized visualization catheter 100 and equivalents thereto utilizes the full area for flow over the majority of length of space-optimized visualization catheter 100. One advantage, among many, to this construction is that it dramatically reduces the overall resistance to flow. Accordingly, the configuration increases flow, when compared to a multi-lumen extrusion with constant cross-section and lumens dedicated to fluid that are sized to meet the most demanding locations along the length of the assembly.

Increasing flow has clinical benefits, but it also may be an advantage in stabilizing or lowering the temperature of CMOS sensor 116. A CMOS sensor that operates at temperatures above the temperature for which it was designed may experience increased noise, which may introduce imaging artifact. Thus, in cases where a CMOS sensor that was designed for use at, for example, room temperature, is selected for use in a medical catheter, which operates at body temperature, an increased flow rate may help reduce imaging artifact via cooling.

FIG. 12 illustrates a perspective view of a second embodiment of space-optimized visualization catheter 1200, FIG. 13 illustrates a perspective view of a second embodiment of camera train holder 1202 for use with space-optimized visualization catheter 1200, and FIG. 14 illustrates a back view of camera train holder 1202. Referring to FIGS. 13-14, camera train holder 1202 holds CMOS sensor 1204 that is square with about 1.8 mm long sides. CMOS sensor 1204 is coupled with lens stack 1206 having about a 1.75 mm diameter. As illustrated in FIG. 12, space-optimized visualization catheter 1200 has a 3.5 mm outer diameter and flattened holder lumen 1208.

Still referring to FIGS. 12-14, camera train holder 1202 is about 2.6 mm in the horizontal direction and about 2.25 mm in the vertical direction. Accordingly, camera train holder 1202 includes an inner surface comprising a circular cross-sectional profile and an outer surface comprising a semi-circular cross-sectional profile such that it includes flattened surface 1210. When compared to conventional holder CH (illustrated in FIGS. 1A-1C) which is 2.6 mm in diameter, camera train holder 1202 has created about 0.35 mm of space in the vertical direction. Thus, the about 0.35 mm space created by flattening top 1210 of camera train holder 1202 is added to working channel 1212.

Alternatively, working channel 1212 could also fit about two 0.5 mm diameter light fibers (not shown) that may be glued or otherwise adhered to the sides of non-round working channel 1212. The utilization of a non-circular cross-sectional profile of camera train holder 1202, such as one having, for example, a semi-circular cross-sectional profile, permits a space-optimized means for holding CMOS sensor 1204 and lens stack 1206.

Camera train holder 1202 and space-optimized visualization catheter 1200 may be constructed efficiently by common materials and methods of construction, including but not limited to, micro-molding, machining, and using numerous materials, including but not limited to, those illustrated in conjunction with other embodiments.

FIG. 15 illustrates a perspective view of another embodiment of space-optimized visualization catheter 1500, FIG. 16 illustrates a perspective view of another embodiment of camera train holder 1600 for use with space-optimized visualization catheter 1500, and FIG. 17 illustrates a cross-sectional perspective view of camera train holder 1600. Illustrative camera train holder 1600 is configured for affixation to distal end 1500b of space-optimized visualization catheter 1500. The camera train holder 1600 may be affixed to distal end 1500b in various ways and/or using various methods, such as welding (e.g., butt welding), reflowing, and/or using one or more mandrels. An illustration of camera train holder 1600 affixed to distal end 1500b is shown in FIG. 17.

Referring to FIGS. 16 and 17, camera train holder 1600 includes channels 1602 for a light (such as four light fibers having a diameter of 0.5 mm diameter lumens on each side of lens stack 1606), working channel port 1604 (such as one configured to have a diameter of about 1 mm), large flush channel 1608, recess (not shown) for holding CMOS sensor 1612 (having dimensions of about 1.8 mm×1.8 mm), and lens stack recess 1610 for holding the components of lens stack 1606. Camera train holder 1600 utilizes round lens 1606 that has been flanked so that it fits within the footprint of CMOS sensor 1612. The flanking of lens stack 1606 optimizes the optical performance of lens stack 1606 and allows for more light to be focused on CMOS sensor 1612. Other configurations are contemplated.

Camera train holder 1600 is joined to space-optimized visualization catheter 1500 in a fashion where the web above lens stack 1606 overlaps the bottom web of working channel 1502 of space-optimized visualization catheter 1500. This overlapping allows for a larger working channel 1502 and allows for flushing around working channel 1502. In addition, as shown in FIG. 17, working channel port 1604 is aligned or substantially aligned with working channel 1502. Another advantage, among many, is that camera train holder 1600 allows the corner of CMOS sensor 1612 to come as close as reasonably possible (about 0.005") to the outside wall of space-optimized visualization catheter 1500.

Thus, camera train holder 1600 reduces the overall footprint by the thickness of the webs located at the top and bottom of lens stack 1606 and thus, allows for a larger working channel 1502 or smaller diameter catheter. The lens stack 1606 maximizes the optical performance while being within the footprint of CMOS sensor 1612 and therefore, it does not limit size of working channel 1604 or increase the diameter of space-optimized visualization catheter 1500. The lens stack 1606 shown in FIG. 17 has a circular cross-sectional profile. In an alternative lens stack configuration, the lens stack 1606 has a square cross-sectional profile. FIG. 17A shows a second alternative lens stack configuration of lens stack 1606A. Lens stack 1606A has two portions, a first portion 1650 having a square cross-sectional profile and a second portion 1652 having a circular cross-sectional profile. In one example of the second alternative configuration, as shown in FIG. 17A, the first portion 1650 having the square cross-sectional profile conforms or substantially conforms to the cross-sectional profile of lens stack recess 1610.

Figure 16A:
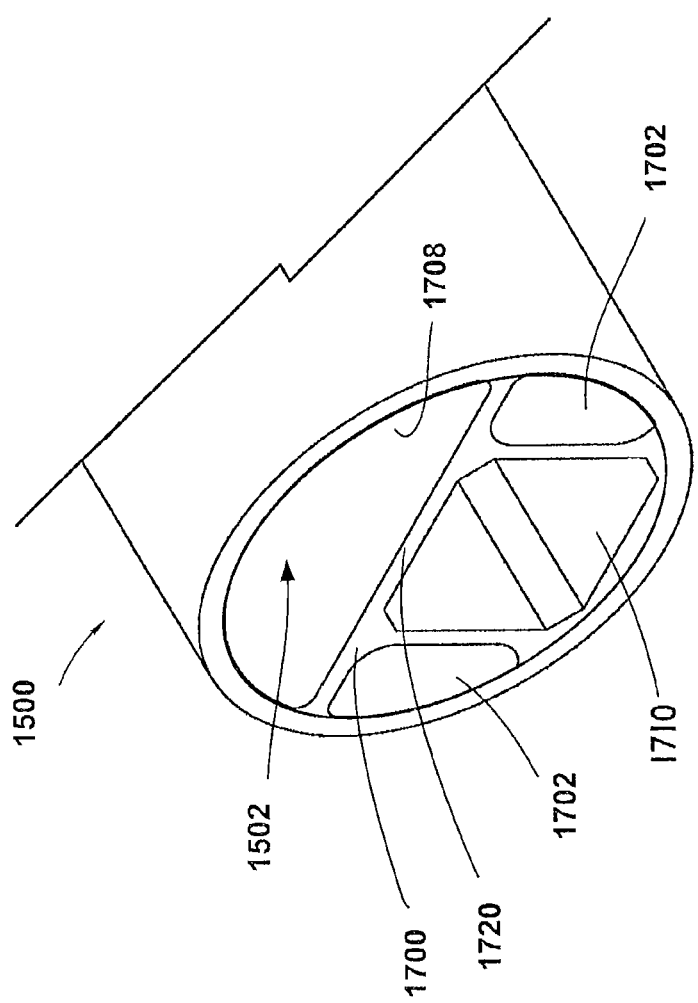
FIG. 16A illustrates a perspective view of an alternate embodiment of the camera train holder for use with the space-optimized visualization catheter illustrated in FIG. 15.

FIG. 16A illustrates a perspective view of an alternate embodiment of camera train holder 1700 for use with space-optimized visualization catheter 1500. In the alternative embodiment, camera train holder 1700 is an insert that is inserted into catheter 1500, such as from distal end 1500b. Inside the catheter, camera train holder insert 1700 is bonded or secured to the inner surface of catheter 1500. Camera train holder insert 1700 includes lens stack recess 1710 similar to lens stack recess 1610 of camera train holder 1600. Camera train holder insert 1700 also includes channels 1702 and large flush channel 1708. Unlike channels 1602 and large flush channel 1608, channels 1702 and large flush channel 1708 are formed in part by an inner surface of catheter 1500.

An upper portion 1720 of camera train holder insert 1700 overlaps or occupies an area that is the same as an area occupied by working channel 1502. So that camera train insert 1700 fits into catheter 1500, a distal portion of a wall of working channel 1502 that extends a longitudinal length of the camera train insert 1700 is removed. In one configuration, as shown in FIG. 16A, all or substantially all of the distal portion of the wall of working channel 1502 is removed. In an alternative configuration, a bottom portion (e.g., only a portion of the wall that is necessary for camera train insert 1700 to fit inside catheter 1500) is removed. The portion of the wall of working channel 1502 that remains helps guide insert 1700 into and/or secure insert 1700 within catheter 1500. In the alternative configuration, a top surface of upper portion 1720 meets or contacts a bottom surface of the wall of working channel 1502. The top surface forms part of working channel 1502 for the longitudinal length of the insert 1700. In alternative configurations, the insert 1700 does not overlap or occupy an area occupied by working channel 1502, in which case no portion of working channel 1502 is removed.

Various configurations similar to camera train holder 1600 or camera train holder 1700, or combinations thereof, are possible. For example, working channel port 1604 of camera train holder 1600 may be included in camera train holder insert 1700 and may meet and/or be aligned with working channel 1502, which has been recessed as previously described.

Space-optimized visualization catheter 1500 and camera train holders 1600, 1700 may be constructed efficiently by common materials and methods of construction, including but not limited to, micro-molding, machining, and using numerous materials, including but not limited to, those illustrated in conjunction with other embodiments.

Considering conventional catheter CC and conventional holder CH illustrated in FIGS. 1A-1C compared to the improved embodiments illustrated in FIGS. 12-17 (assuming all walls are at least 0.005" thick and the outer diameter of the catheter is fixed at 3.5 mm) the working channel is effected in size in the following manner: conventional catheter CC and conventional holder CH (illustrated in FIGS. 1A-1C) provide a maximum working channel size of 0.52 mm, while space-optimized visualization catheter 1200 and camera train holder 1202 (illustrated in FIGS. 12-14) provide a maximum working channel size of about 0.86 mm (a 65% increase in diameter from conventional catheter CC and conventional holder CH), and space-optimized visualization catheter 1500 and camera train holder 1600 (illustrated in FIGS. 15, 16, and 17) provide a maximum working channel size of about 0.98 mm (an 88% increase in diameter from conventional catheter CC and conventional holder CH).

Figure 19:
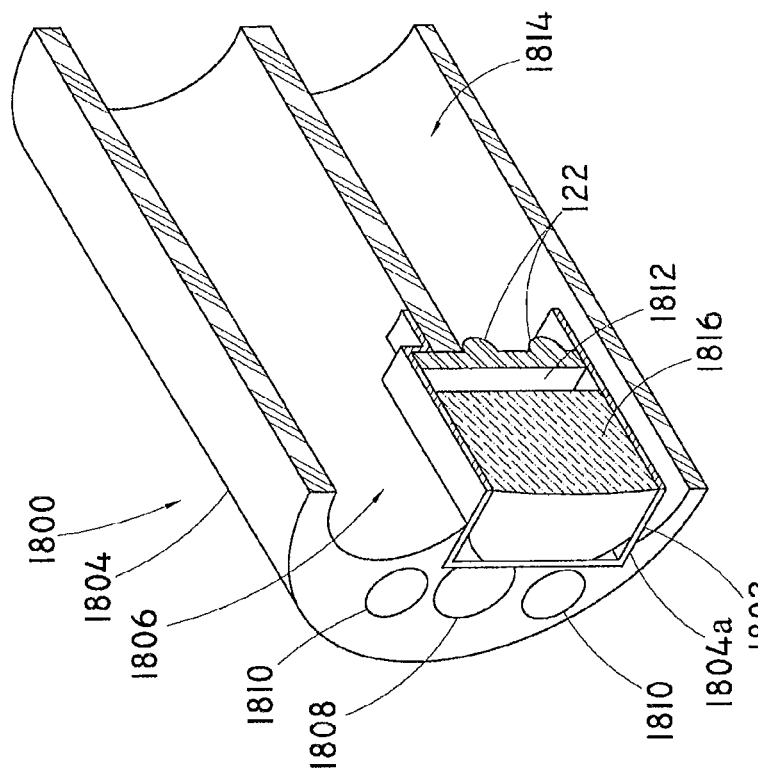
FIG. 19 illustrates a cross-sectional perspective view of the space-optimized visualization catheter illustrated in FIG. 18.
Figure 18:
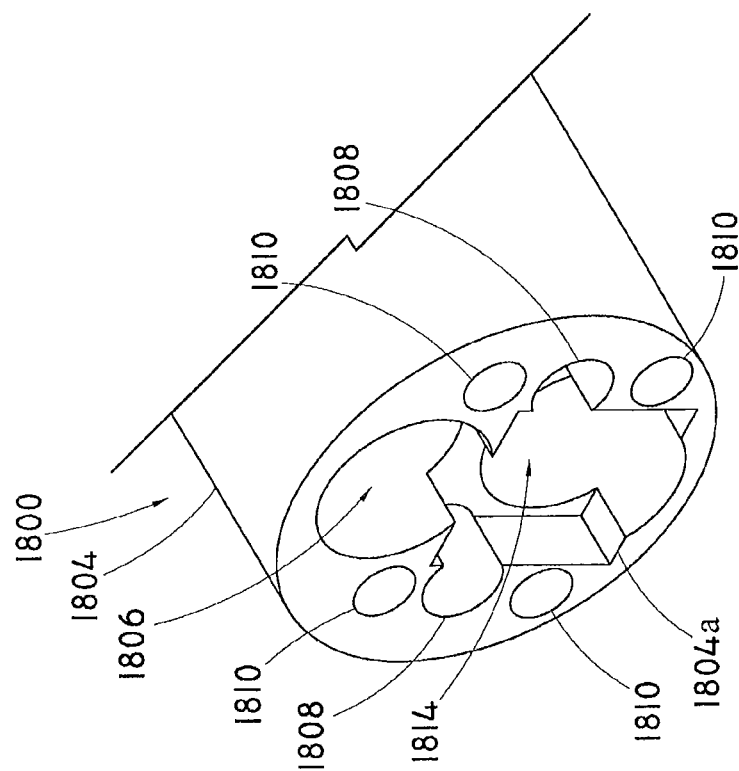
FIG. 18 illustrates a perspective view of another embodiment of a space-optimized visualization catheter.

FIG. 18 illustrates a perspective view of another embodiment of space-optimized visualization catheter 1800, FIG. 19 illustrates a cross-sectional perspective view of space-optimized visualization catheter 1800, and FIG. 20 illustrates a schematic view of space-optimized visualization catheter 1800. Referring to FIGS. 18-20, space-optimized catheter 1800 preferably comprises an extruded catheter body 1804 which is modified by means of a secondary operation to receive camera train holder 1802. Catheter body 1804 is extruded with working channel 1806, two light lumens 1808, four fluid lumens 1810, and cabling lumen 1814, although other configurations are contemplated.

Camera train holder 1802 is preferably a square holder having ultra-thin walls that are about 0.003" thick, although other configurations are contemplated. Camera train holder 1802 is joined to catheter body 1804 such that the placement of lumens of catheter body 1804 are configured to maximize the diameter of working channel 1806 for the entire length of space-optimized visualization catheter 1800 with the exception being the most distal tip. For example, catheter body 1804 is composed of cabling lumen 1814 having a diameter of about 1.8 mm and working channel lumen 1806 having a diameter of about 1.2 mm. The three webs that lie along a line connecting lumens are about 0.005" thick.

The secondary operation removes square notch 1804a which is slightly larger (in order to accommodate camera train holder 1802) than the 1.8 mm×1.8 mm square CMOS sensor 1812. Square notch 1804a is off-center of cabling lumen 1814. CMOS sensor 1812, lens stack 1816, and sensor cabling (not shown) are loaded into camera train holder 1802. Camera train holder 1802 is then back-loaded into square notch 1804a of catheter body 1804 so that cabling (not shown) is fed through cabling lumen 1814. Due to the off-centering of square notch 1804a, the cabling (not shown) is directed down between the transition between camera train holder 1802 and catheter body 1804. This slight off-centering of cabling lumen 1814 opens up space so that the diameter of working channel 1806 may be maximized. Thus, the smaller the cabling diameter, the larger working channel 1806 may be configured. In this embodiment, for example, cabling is assumed to have a diameter of just less than 1.8 mm, and working channel 1806 is maximized to be 1.2 mm for the entire length of catheter body 1804 with the exception of the last 7.5 mm where working channel 1806 is about 0.96 mm in diameter. The off-centering of cabling lumen 1814 with respect to camera train holder 1802 maximizes the diameter of working channel 1806 for the vast majority of the length of space-optimized catheter 1800.

Space-optimized visualization catheter 1800 and equivalents thereto may be constructed efficiently by common materials and methods of construction, including but not limited to, micro-molding, machining, and using numerous materials, including but not limited to, those illustrated in conjunction with other embodiments.

FIG. 20A illustrates a perspective view of an alternate embodiment of space-optimized visualization catheter 2100, and FIG. 20B illustrates a cross-sectional perspective view of the same. Referring to FIGS. 20A-20B, catheter 2000 is similar to catheter 1800 (illustrated in FIGS. 18-20), and camera train holder 2002 is similar to camera train holder 1802 (illustrated in FIGS. 18-20) in terms of construction, method of use, and assembly. Space-optimized catheter 2000 preferably comprises an extruded catheter body 2004 which is modified by means of a secondary operation to receive camera train holder 2002—similar to the means illustrated in conjunction with space-optimized visualization catheter 1800.

Catheter body 2004 is extruded with working channel 2006, two light lumens 2008, two fluid lumens 2010, and cabling lumen 2014, although other configurations are contemplated. Camera train holder 2002 is preferably a square holder having ultra-thin walls that are about 0.003" thick, although other configurations are contemplated. Camera train holder 2002 is joined to catheter body 2004 such that the placement of lumens of catheter body 2004 are configured to maximize the diameter of working channel 2006 for the entire length of space-optimized visualization catheter 2000 with the exception being the most distal tip.

The secondary operation removes square notch 2004a which is slightly larger (in order to accommodate camera train holder 2002) than the 1.8 mm×1.8 mm square CMOS sensor 2012. Square notch 2004a is off-center of cabling lumen 2014. CMOS sensor 2012, lens stack 2016, and sensor cabling (not shown) are loaded into camera train holder 2002. Camera train holder 2002 is then back-loaded into square notch 2004a of catheter body 2004 so that cabling (not shown) is fed through cabling lumen 2014. Due to the off-centering of square notch 2004a, the cabling (not shown) is directed down between the transition between camera train holder 2002 and catheter body 2004. This slight off-centering of cabling lumen 2014 opens up space so that the diameter of working channel 2006 may be maximized. Thus, the smaller the cabling diameter, the larger working channel 2006 may be configured.

Space-optimized visualization catheter 2000 and equivalents thereto may be constructed efficiently by common materials and methods of construction, including but not limited to, micro-molding, machining, and using numerous materials, including but not limited to, those illustrated in conjunction with other embodiments.

Figure 23:
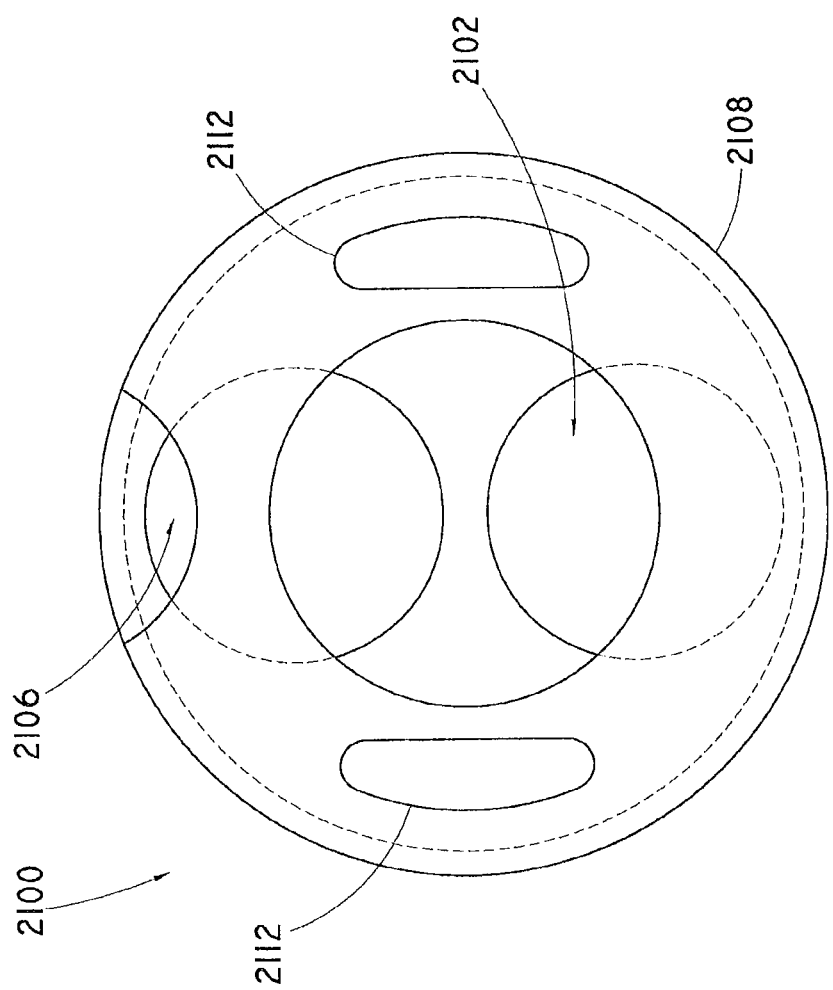
FIG. 23 illustrates a front view of the space-optimized visualization catheter illustrated in FIG. 21.

FIG. 21 illustrates a perspective view of another embodiment of a space-optimized visualization catheter 2100, FIG. 22 illustrates a cross-sectional perspective view of space-optimized visualization catheter 2100, and FIG. 20 illustrates a front view of space-optimized visualization catheter 2100. Referring to FIGS. 21-23, space-optimized catheter 2100 is constructed in a manner similar to space-optimized catheter 1800 (illustrated in FIGS. 18-20), wherein cabling lumen 2102 is off-center and the cable (not shown) is disposed down from CMOS sensor 2104 into cabling lumen 2102. Catheter body 2108 also includes light lumens 2112.

CMOS sensor 2104, lens stack 2114, and sensor cabling (not shown) are loaded into camera train holder 2110. Camera train holder 2110 is then back-loaded into the square notch 2108a of catheter body 2108 so that cabling (not shown) is fed through cabling lumen 2102.

Space-optimized visualization catheter 2100 includes working channel 2106 that exits at the side of catheter body 1208 so that working channel 2106 having a maximized diameter may be fully utilized. The size of working channel 2106 is primarily dependent on the size of the cabling (not shown) attached to CMOS sensor 2104. For example, the cabling for this particular embodiment is about 1.4 mm in diameter and therefore cabling lumen 2102 is oversized to have a diameter of about 1.5 mm to accept the smaller cable. With cabling lumen 2102 having a diameter of about 1.5 mm and catheter body 1208 having an outer diameter of about 3.5 mm as a constraint, working channel 1206 may be maximized to a diameter of about 1.6 mm. With side port 1206a of working channel 1206 that exits at 10 mm or less from the distal tip, the configuration allows full utilization of the entirety of the 1.6 mm diameter working channel 1206 for an endoscopic accessory. This 1.6 mm diameter working channel 1206 is at least 60% larger than any lumen that exits at the distal tip when utilizing a typical 1.8 mm×1.8 mm CMOS sensor. Another advantage, among many, of this configuration is that distal tip of catheter body 2108 is tapered and therefore it should be easier to gain access to an orifice due to a smaller diameter tip. The off-centering of cabling lumen 2102 with respect to camera train holder 2110 maximizes the diameter of working channel 2106 for the vast majority of the length of space-optimized visualization catheter 2100. The side exiting 2106a working channel 2106 when used in conjunction with camera train holder 2110 maximizes the diameter of working channel 2106 and therefore allows for larger accessories.

Space-optimized visualization catheter 2100 and equivalents thereto may be constructed efficiently by common materials and methods of construction, including but not limited to, micro-molding, machining, and using numerous materials, including but not limited to, those illustrated in conjunction with other embodiments.

Figure 24:
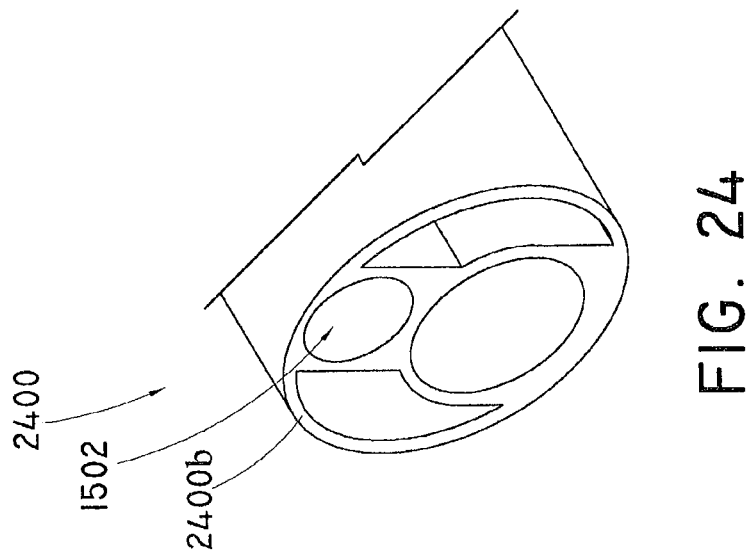
FIG. 24 illustrates a perspective view of another embodiment of a space-optimized visualization catheter.
Figure 26:
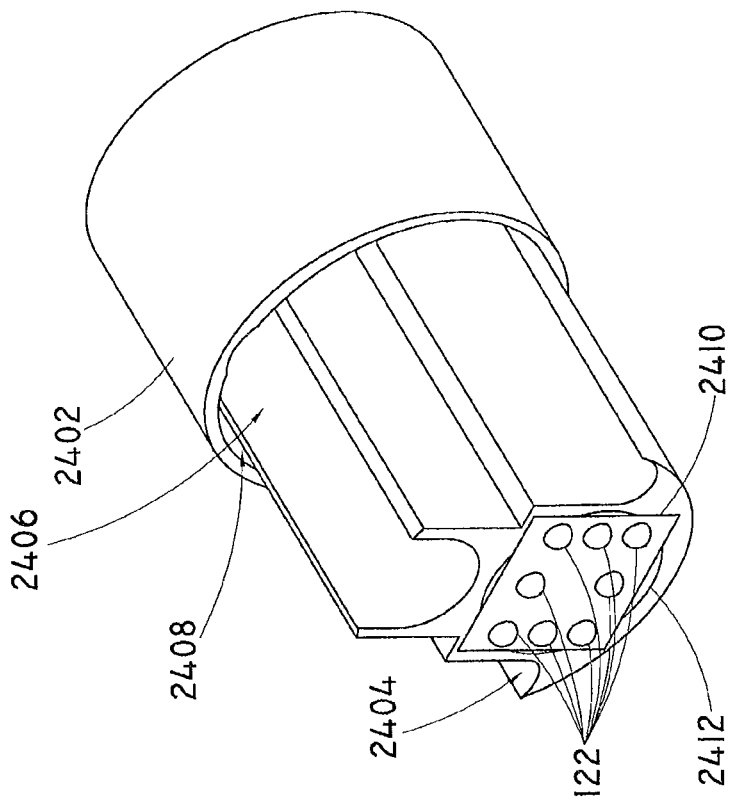
FIG. 26 illustrates a perspective back-view of the camera train holder illustrated in FIG. 25.
Figure 25:
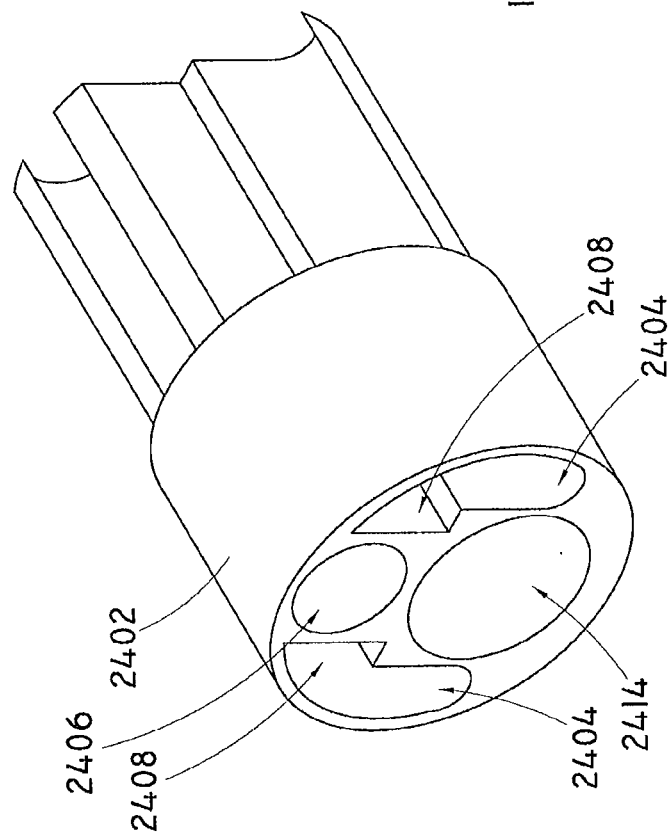
FIG. 25 illustrates a perspective view of a camera train holder for use with the space-optimized visualization catheter illustrated in FIG. 24.

FIG. 24 illustrates a perspective view of another embodiment of space-optimized visualization catheter 2400, FIG. 25 illustrates a perspective view of camera train holder 2402 for use with space-optimized visualization catheter 2400, and FIG. 26 illustrates a perspective back-view of camera train holder 2402. Referring to FIGS. 24-26, catheter 2400 is similar to catheter 1500 (illustrated in FIG. 15), and camera train holder 2402 is similar to camera train holder 1600 (illustrated in FIGS. 16 and 17) in terms of construction, method of use, and assembly. Camera train holder 2402 is configured for affixation to distal end 2400b of space-optimized visualization catheter 2402. Camera train holder 2402 includes channels 2404 for a light, working channel port 2406, flush channel 2408, recess (not shown) for holding CMOS sensor 2410 (having dimensions of about 1.8 mm×1.8 mm), and lens stack recess 2412 for holding the components of lens stack 2414. Camera train holder 2402 utilizes round lens 2414 that has been flanked so that it fits within the footprint of CMOS sensor 2410. The flanking of lens stack 2414 optimizes the optical performance of lens stack 2414 and allows for more light to be focused on CMOS sensor 2410. Camera train holder 2402 is joined to space-optimized visualization catheter 2400 such that camera train holder 2402 is a separate component part insertable into space-optimized visualization catheter 2400 as with camera train holder 1600 (illustrated in FIGS. 16 and 17).

Space-optimized visualization catheter 2400 and equivalents thereto may be constructed efficiently by common materials and methods of construction, including but not limited to, micro-molding, machining, and using numerous materials, including but not limited to, those illustrated in conjunction with other embodiments.

FIG. 27 illustrates a perspective view of another embodiment of space-optimized visualization catheter 2700, FIG. 28 illustrates a schematic view of space-optimized visualization catheter 2700, and FIG. 29 illustrates space-optimized visualization catheter 2700 in use. Referring to FIGS. 27-29, space-optimized visualization catheter 2700 has a non-circular cross-sectional profile. Space-optimized visualization catheter 2700 is similar to other space-optimized visualization catheter embodiments illustrated herein and equivalents thereto in terms of construction and assembly. Space-optimized visualization catheter 2700 includes working channel 2702, two light lumens 2704, two flushing lumens 2706, and camera train holder 2708 configured for holding lens stack 2710 and CMOS sensor (not shown). Camera train holder 2708 is similar to other camera train holders illustrated herein and equivalents thereto.

Space-optimized visualization catheter 2700 is configured for use with duodenoscope 2800 equipped with a side-exiting accessory elevator 2802. Elevator 2802 of duodenoscope 2800 limits the size of a circular catheter to less than 3.5 mm. However, accessory channel 2804 of duodenoscope 2800 has a diameter of 4.2 mm. Thus, by using accessory channel's elevator 2802, there is a loss of 0.7 mm from the space available in accessory channel 2804 versus that available at the accessory channel's elevator site 2802. Presently, manufacturers would attempt to reduce the overall size of a round catheter to less than 3.5 mm to fit through elevator site 2802. However, space-optimized visualization catheter 2700 optimizes space by having a non-circular, oblong, cross-sectional profile. Thus, space-optimized visualization catheter 2700 may be limited to 3.5 mm on one side and up to 4.2 mm on the orthogonal side. Accordingly, a larger device is able to be utilized through accessory channel's elevator 2402.

For example, a 1.5 mm and 1.7 mm forceps and basket may be directed through working channel lumen 2702 of space-optimized visualization catheter 2700 due to the increase in the size of working channel lumen 2702. For example, using a 1.8 mm×1.8 mm CMOS sensor 2410, if the embodiment illustrated in FIGS. 27-28 were to have a circular cross-sectional profile (as opposed to being having an oblong cross-sectional profile), the working channel lumen would be limited to 1 mm. However, because space-optimized visualization catheter 2700 has an oblong cross-sectional profile, a 1.75 mm working channel lumen 2702 is achieved. As such, a diameter of working channel lumen 2702 of space-optimized visualization catheter 2700 is increased by 75% compared to typical catheters for disposal through accessory channel 2804 of duodenoscope 2800.

Space-optimized visualization catheter 2700 and equivalents thereto may be constructed efficiently by common materials and methods of construction, including but not limited to, micro-molding, machining, and using numerous materials, including but not limited to, those illustrated in conjunction with other embodiments.

Space-optimized visualization catheters illustrated herein and equivalents thereto may further comprise one or more rigid portions and one or more portions more flexible than the one or more rigid portions. For example, a rigid portion of a space-optimized visualization catheter may include a portion of an outer sheath configured for receiving a camera train holder. The one or more flexible portions may be configured to aid in steering. For example, the one or more flexible portions may comprise one or more vertebrae modules. Alternatively, the one or more flexible portions may comprise ribs. Alternatively, the one or more flexible portions may comprise grooves or cuts made into the same material as that of the one or more rigid portions. Alternatively, space-optimized visualization catheters illustrated herein and equivalents thereto may be configured with a first rigid portion for accepting a camera train holder, a second portion configured for flexibility and steering ease, and a third portion configured similar to a standard flexible catheter. Alternatively, space-optimized visualization catheters illustrated herein and equivalents thereto may be configured with a soft portion and a rigid portion, wherein the interiors of each section change throughout the device to aid with steering or to achieve other benefits.

From the foregoing, the discovery of methods and apparatuses of space-optimized visualization catheters provides numerous benefits to the medical field. It can be seen that the embodiments illustrated and equivalents thereto as well as the methods of manufacturer may utilize machines or other resources, such as human beings, thereby reducing the time, labor, and resources required to manufacturer the embodiments. Indeed, the discovery is not limited to the embodiments illustrated herein, and the principles and methods illustrated herein can be applied and configured to any catheter and equivalents.

Those of skill in the art will appreciate that embodiments not expressly illustrated herein may be practiced within the scope of the present discovery, including that features illustrated herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages illustrated above are not necessarily the only advantages of the discovery, and it is not necessarily expected that all of the illustrated advantages will be achieved with every embodiment of the discovery.

What is claimed is:

1. A visualization catheter comprising:
 a camera train holder holding a camera train comprising a visualization sensor and a lens stack; and
 a catheter comprising:
  a proximal catheter portion;
  a distal catheter portion;
  a working channel lumen extending through the proximal catheter portion and the distal catheter portion;
  a cabling lumen extending through the proximal catheter portion and the distal catheter portion and adjacent to the working channel lumen, wherein the cabling lumen is configured to have disposed therein cabling that is electrically coupled to the visualization sensor at a distal end of the cabling lumen; and
  a notch having disposed therein the camera train holder, wherein the notch is disposed into an inner surface of the distal catheter portion, and wherein the notch is positioned distal the distal end of the cabling lumen and axially off-centered from a central longitudinal axis of the cabling lumen at the distal end of the cabling lumen.

2. The visualization catheter of claim 1, wherein a proximal camera train holder portion of the camera train holder holds the visualization sensor.

3. The visualization catheter of claim 2, wherein the visualization sensor comprises a CMOS sensor.

4. The visualization catheter of claim 1, wherein a distal camera train holder portion of the camera train holder holds the lens stack.

5. The visualization catheter of claim 1, wherein the catheter further comprises a light lumen extending through the proximal catheter portion and the distal catheter portion.

6. The visualization catheter of claim 1, wherein the catheter further comprises a fluid lumen extending through the proximal catheter portion and the distal catheter portion.

7. The visualization catheter of claim 1, wherein the working channel is configured to exit at a distal side portion of the catheter.

8. The visualization catheter of claim 1, wherein the distal catheter portion is tapered.

9. The visualization catheter of claim 1, wherein the distal catheter portion is tapered; and wherein the working channel is configured to exit at a side portion of the catheter proximal to the taper.

10. A visualization catheter comprising:
a camera train holder having disposed therein a camera train comprising a visualization sensor and a lens stack; and
a catheter comprising:
a proximal catheter portion;
a distal catheter portion comprising a taper;
a working channel lumen extending through the proximal catheter portion and the distal catheter portion, wherein the working channel exits at a side of the catheter;
a cabling lumen extending through the proximal catheter portion and the distal catheter portion and adjacent to the working channel lumen, wherein the cabling lumen is configured to have disposed therein cabling that is electrically coupled to the visualization sensor at a distal end of the cabling lumen; and
a notch having disposed therein the camera train holder, wherein the notch is disposed into an inner surface of the distal catheter portion, and wherein the notch is positioned distal the cabling lumen and axially off-centered from a central longitudinal axis of the cabling lumen at the distal end of the cabling lumen.

11. The visualization catheter of claim 10, wherein the visualization sensor is disposed within a proximal camera train holder portion of the camera train holder.

12. The visualization catheter of claim 11, wherein the visualization sensor comprises a CMOS sensor.

13. The visualization catheter of claim 10, wherein the lens stack is disposed within a distal camera train holder portion of the camera train holder.

14. The visualization catheter of claim 10, wherein the catheter further comprises a light lumen extending through the proximal catheter portion and the distal catheter portion.

15. The visualization catheter of claim 10, wherein the catheter further comprises a fluid lumen extending through the proximal catheter portion and the distal catheter portion.

16. The visualization catheter of claim 10, wherein the working channel is configured to exit at a location proximal to the taper.

17. A method of manufacturing a visualization catheter comprising:
extruding a catheter comprising:
a proximal catheter portion;
a distal catheter portion;
a working channel lumen extending through the proximal catheter portion and the distal catheter portion;
a cabling lumen extending through the proximal catheter portion and the distal catheter portion and adjacent to the working channel lumen; and
forming a notch sized to hold a camera train holder that holds a camera train comprising a visualization sensor and a lens stack, the notch formed in an inner surface of the distal catheter portion, wherein the notch, when formed in the inner surface, is positioned distal the distal end of the cabling lumen and axially off-centered from a central longitudinal axis of the cabling lumen at the distal end of the cabling lumen; and
placing the camera train holder into the notch.

18. The method of claim 17, further comprising coupling the visualization sensor to a proximal camera train holder portion of the camera train holder.

19. The method of claim 17, further comprising coupling the lens stack to a distal camera train holder portion of the camera train holder.

20. The method of claim 17, further comprising directing an electrical cable through the cabling lumen of the catheter.

* * * * *